(12) United States Patent
Klingemann et al.

(10) Patent No.: US 12,180,283 B2
(45) Date of Patent: Dec. 31, 2024

(54) ANTI-B7-H4 CHIMERIC ANTIGEN RECEPTOR-MODIFIED NK-92 CELLS

(71) Applicant: ImmunityBio, Inc., Culver City, CA (US)

(72) Inventors: Hans G. Klingemann, Culver City, CA (US); Laurent H. Boissel, Culver City, CA (US)

(73) Assignees: ImmunityBio, Inc.; Culver City, Inc.

(*) Notice: Subject to any disclaimer, the term of this patent is extended or adjusted under 35 U.S.C. 154(b) by 307 days.

(21) Appl. No.: 17/287,462

(22) PCT Filed: Aug. 1, 2019

(86) PCT No.: PCT/US2019/044719
§ 371 (c)(1),
(2) Date: Apr. 21, 2021

(87) PCT Pub. No.: WO2021/021213
PCT Pub. Date: Feb. 4, 2021

(65) Prior Publication Data
US 2022/0144952 A1    May 12, 2022

(51) Int. Cl.
| C07K 16/28 | (2006.01) |
| A61K 35/17 | (2015.01) |
| A61K 45/06 | (2006.01) |
| A61P 35/00 | (2006.01) |
| C07K 14/54 | (2006.01) |
| C07K 14/55 | (2006.01) |
| C07K 14/705 | (2006.01) |
| C07K 14/725 | (2006.01) |
| C07K 14/735 | (2006.01) |

(52) U.S. Cl.
CPC .......... *C07K 16/2827* (2013.01); *A61K 35/17* (2013.01); *A61K 45/06* (2013.01); *A61P 35/00* (2018.01); *C07K 14/5443* (2013.01); *C07K 14/55* (2013.01); *C07K 14/7051* (2013.01); *C07K 14/70517* (2013.01); *C07K 14/70521* (2013.01); *C07K 14/70535* (2013.01); *C07K 2317/622* (2013.01); *C07K 2319/03* (2013.01)

(58) Field of Classification Search
CPC ............ C07K 16/2827; C07K 14/5443; C07K 14/55; C07K 14/7051; C07K 14/70517; C07K 14/70521; C07K 14/70535; C07K 2317/622; C07K 2319/03; C07K 16/2803; C07K 2317/73; C07K 2319/33; A61K 35/17; A61K 45/06; A61K 39/4613; A61K 39/4631; A61K 39/464402; A61K 2239/22; A61K 39/464411; A61K 39/464412; A61P 35/00; C12N 5/0646; C12N 2501/515; C12N 2510/00
See application file for complete search history.

(56) References Cited

U.S. PATENT DOCUMENTS

| 7,618,817 | B2 | 11/2009 | Campbell | |
| 8,034,332 | B2 | 10/2011 | Klingemann | |
| 8,313,943 | B2 | 11/2012 | Campbell | |
| 9,150,636 | B2 | 10/2015 | Campbell | |
| 9,181,322 | B2 | 11/2015 | Campbell | |
| 10,138,462 | B2 | 11/2018 | Klingemann | |
| 11,547,727 | B2 * | 1/2023 | Boissel | C07K 16/2827 |
| 11,643,452 | B2 * | 5/2023 | Boissel | A61K 31/12 424/93.21 |
| 2008/0247990 | A1 | 10/2008 | Campbell | |
| 2013/0280285 | A1 | 10/2013 | Schonfeld et al. | |
| 2014/0242701 | A1 | 8/2014 | Shiku et al. | |
| 2014/0255363 | A1 | 9/2014 | Metelitsa et al. | |
| 2014/0274909 | A1 | 9/2014 | Orentas et al. | |
| 2016/0361360 | A1 | 12/2016 | Chang et al. | |
| 2018/0118831 | A1 | 5/2018 | Epstein et al. | |
| 2018/0353544 | A1 | 12/2018 | Rezvani et al. | |

(Continued)

FOREIGN PATENT DOCUMENTS

| CN | 107531782 A | 1/2018 |
| CN | 107709552 A | 2/2018 |
| CN | 109804064 A | 5/2019 |

(Continued)

OTHER PUBLICATIONS

Haynes et al., Redirecting Mouse CTL Against Colon Carcinoma: Superior Signaling Efficacy of Single-Chain Variable Domain Chimeras Containing TCR-ζ vs FcεRI-γγ, The Journal of Immunology, 2001, vol. 166, No. 1, pp. 182-187 (Cited from Specification).
Cartellieri et al., "Chimeric antigen receptor-engineered T cells for immunotherapy of cancer", Journal of Biomedicine and Biotechnology, 2010, vol. 2010, No. 956304, pp. 1-13 (Cited from Specification).
Hermanson et al., "Utilizing chimeric antigen receptors to direct natural killer cell activity", Frontiers in Immunology, 2015, vol. 6, No. 195, pp. 1-6 (Cited from Specification).
Bollino et al., "Chimeric antigen receptor-engineered natural killer and natural killer T cells for cancer immunotherapy", Transl. Res., Sep. 2017, vol. 187, 21 pages (Cited from Specification).

(Continued)

*Primary Examiner* — Brad Duffy
*Assistant Examiner* — Amber K Faust
(74) *Attorney, Agent, or Firm* — Umberg Zipser LLP

(57) ABSTRACT

Recombinant NK cells, and particularly recombinant NK-92 cells express an anti-B7-H4 chimeric antigen receptor (CAR) having an intracellular domain of FcεRIγ. Most notably, CAR constructs with an intracellular domain of FcεRIγ had a significantly extended duration of expression and cytotoxicity over time. The anti-B7-H4 CAR may be expressed from RNA and DNA, preferably from a tricistronic construct that further encodes CD16 and a cytokine to confer autocrine growth support. Advantageously, such constructs also enable high levels of transfection and expression of the recombinant proteins and provide a convenient selection marker to facilitate rapid production of recombinant NK/NK-92 cells.

21 Claims, 9 Drawing Sheets
Specification includes a Sequence Listing.

(56) References Cited

U.S. PATENT DOCUMENTS

2021/0347850 A1* 11/2021 Boissel .................. C07K 16/32

FOREIGN PATENT DOCUMENTS

| IL | 278857 A | 1/2021 | |
|---|---|---|---|
| WO | WO-2004013276 A2 * | 2/2004 | ............. C07K 16/00 |
| WO | 2006/023148 A2 | 3/2006 | |
| WO | 2013/040371 A2 | 3/2013 | |
| WO | 2014/039523 A1 | 3/2014 | |
| WO | 2014/099671 A1 | 6/2014 | |
| WO | 2016/160620 A2 | 10/2016 | |
| WO | 2016/201304 A1 | 12/2016 | |
| WO | 2017/112877 A1 | 6/2017 | |
| WO | 2018/076391 A1 | 5/2018 | |
| WO | 2019/226708 A1 | 11/2019 | |
| WO | 2021/021213 A1 | 2/2021 | |

OTHER PUBLICATIONS

Konstantinidis et al., "Targeting IL-2 to the endoplasmic reticulum confines autocrine growth stimulation to NK-92 cells", Experimental Hematology, 2005, vol. 33, pp. 159-164 (Cited from Specification).

Gong et al., "Characterization of a human cell line (NK-92) with phenotypical and functional characteristics of activated natural killer cells", Leukemia, Apr. 1994, vol. 8, No. 4, pp. 652-658 (Cited from Specification).

Bruhns et al., "Specificity and affinity of human Fcgamma receptors and their polymorphic variants for human IgG subclasses", Blood, vol. 113, No. 16, pp. 3716-3725 (Cited from Specification).

Jochems et al., "An NK cell line (haNK) expressing high levels of granzyme and engineered to express the high affinity CD16 allele", Oncotarget, 2016, vol. 7, No. 52, pp. 86359-86373 (Cited from Specification).

Garcia-Sanchez et al., "Cytosine deaminase adenoviral vector and 5-fluorocytosine selectively reduce breast cancer cells 1 million-fold when they contaminate hematopoietic cells: a potential purging method for autologous transplantation", Blood, 1998, vol. 92, No. 2, pp. 672-682 (Cited from Specification).

Touati et al., "A suicide gene therapy combining the improvement of cyclophosphamide tumor cytotoxicity and the development of an anti-tumor immune response", Current Gene Therapy, 2014, vol. 14, pp. 236-246 (Cited from Specification).

Di Stasi et al., "Inducible apoptosis as a safety switch for adoptive cell therapy", N Engl J Med., Nov. 3, 2011, vol. 365, No. 18, pp. 1673-1683 (Cited from Specification).

Morgan Richard A, "Live and Let Die: A New Suicide Gene Therapy Moves to the Clinic", Molecular therapy, Jan. 2012, vol. 20, No. 1, pp. 11-13 (Cited from Specification).

Smith et al., "Comparison of Biosequences", Advances in applied mathematics, 1981, vol. 2, pp. 482-489 (Cited from Specification).

Altschul et al., "Gapped Blast and PSI-Blast: A new generation of protein database search programs", Nucleic Acids Research, 1997, vol. 25, No. 17, pp. 3389-3402 (Cited from Specification).

Altschul et al., "Basic Local Alignment Tool", J. Mol. Biol., 1990, vol. 215, pp. 403-410 (Cited from Specification).

Henikoff et al., "Amino acid substitution matrices from protein blocks", Biochemistry, Proc. Natl. Acad. Sci. USA, Nov. 1992, vol. 89, Pp. 10915-10919 (Cited from Specification).

Yazawa et al., "Current Progress in Suicide gene therapy for cancer", World J. Surg. Jul. 2002; 26(7): 783-9 (Cited from Specification).

International Search Report and Written Opinion received for International PCT Application Serial No. PCT/US2019/044719 dated May 1, 2020, 12 pages.

Li et al., "Co-inhibitory Molecule B7 Superfamily Member 1Expressed by Tumor-Infiltrating Myeloid CellsInduces Dysfunction of Antitumor CD8+ T Cells", Immunity, 2018, vol. 48, pp. 1-14.

First Office Action received for Chinese Patent Application Serial No. 201980078441.4 dated Aug. 5, 2023, 17 pages. (Including English Translation).

Office Action received for Canadian Patent Application Serial No. 3,115,917 dated Mar. 29, 2022, 8 pages.

International Preliminary Report on Patentability received for PCT Application Serial No. PCT/US2019/044719 dated Feb. 10, 2022, 8 pages.

Examination Report No. 1 received for Australian Patent Application Serial No. 2019459423 dated Sep. 23, 2022, 5 pages.

Examination Report No. 2 received for Australian Patent Application Serial No. 2019459423 dated Apr. 24, 2023, 2 pages.

Examination Report No. 3 received for Australian Patent Application Serial No. 2019459423 dated May 1, 2023, 2 pages.

Office Action received for Canadian Patent Application Serial No. 3,115,917 dated Mar. 6, 2023, 6 pages.

Extended European Search Report received for the EP Patent Application Serial No. 19939678.9 dated Jan. 24, 2023, 9 pages.

Notice of Acceptance of Application received for Australian Patent Application Serial No. 2019459423 dated May 17, 2023, 3 pages.

Office Action received for Israel Patent Application Serial No. 283568 dated May 1, 2023, 13 pages. (Including English Translation).

First Substantive Examination Report received for Israel Patent Application Serial No. 283568 dated Feb. 20, 2022, 14 pages. (Including English Translation).

Zhang et al., "Chimeric Antigen Receptor-Engineered NK-92 Cells: An Off-the-Shelf Cellular Therapeutic for Targeted Elimination of Cancer Cells and Induction of Protective Antitumor Immunity", Frontiers in Immunology, Hypothesis and Theory, vol. 8, Article 533, May 18, 2017, pp. 1-17.

Search Report and Written Opinion received for Singapore Patent Application Serial No. 11202103981X dated Jun. 14, 2022, 8 pages.

* cited by examiner

SEQUENCE LISTING

<160> NUMBER OF SEQ ID NOS: 30

<210> SEQ ID NO 1
<211> LENGTH: 405
<212> TYPE: PRT
<213> ORGANISM: Artificial Sequence
<220> FEATURE:
<223> OTHER INFORMATION: Anti-B7-H4 CAR

<400> SEQUENCE: 1

```
Met Asp Trp Ile Trp Arg Ile Leu Phe Leu Val Gly Ala Ala Thr Gly
1               5                   10                  15

Ala His Ser Ala Gln Pro Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Thr Phe Asn Ser Tyr Ala Met His Trp Val Arg Gln Ala Pro
        50                  55                  60

Gly Lys Gly Leu Glu Trp Val Ser Ala Ile Ser Gly Asn Gly Gly Ser
65                  70                  75                  80

Thr Arg Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Asp Arg Phe Arg Lys Val His
        115                 120                 125

Gly Phe Asp Val Trp Gly Gln Gly Thr Leu Val Thr Val Ser Ser Gly
    130                 135                 140

Gly Gly Gly Ser Gly Gly Gly Ser Gly Gly Gly Ser Gly
145                 150                 155                 160

Gly Gly Asp Ile Gln Met Thr Gln Ser Pro Ser Ser Leu Ser Ala Ser
                165                 170                 175

Val Gly Asp Arg Val Thr Ile Thr Cys Gln Ala Ser Gln Asp Ile Ser
            180                 185                 190

Asn Tyr Leu Asn Trp Tyr Gln Gln Lys Pro Gly Lys Ala Pro Lys Leu
        195                 200                 205

Leu Ile Tyr Asp Ala Ser Asn Leu Glu Thr Gly Val Pro Ser Arg Phe
    210                 215                 220

Ser Gly Ser Gly Ser Gly Thr Asp Phe Thr Phe Thr Ile Ser Ser Leu
225                 230                 235                 240

Gln Pro Glu Asp Ile Ala Thr Tyr Tyr Cys Gln Gln Asp Ala Thr Phe
                245                 250                 255

Pro Leu Thr Phe Gly Gln Gly Thr Lys Val Glu Ile Lys Ala Ala Ala
            260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
            340                 345                 350

Leu Val Thr Val Ala Phe Ile Ile Phe Trp Val Arg Leu Lys Ile Gln
```

```
                    355                 360                 365
Val Arg Lys Ala Ala Ile Thr Ser Tyr Glu Lys Ser Asp Gly Val Tyr
        370                 375                 380

Thr Gly Leu Ser Thr Arg Asn Gln Glu Thr Tyr Glu Thr Leu Lys His
385                 390                 395                 400

Glu Lys Pro Pro Gln
            405

<210> SEQ ID NO 2
<211> LENGTH: 1215
<212> TYPE: DNA
<213> ORGANISM: Artificial Sequence
<220> FEATURE:
<223> OTHER INFORMATION: anti-B7-H4 CAR (nucleic acid sequence)

<400> SEQUENCE: 2
atggactgga tctggcggat tctgtttctc gtgggagctg ccacaggcgc tcattctgct      60
cagcctgccg aagttcagct tgtagaatct ggaggtggat tggttcaacc tggtggctct     120
cttcgcctga gttgtgcagc tctggttttt actttcaata gttacgctat gcattgggtt     180
cgtcaggctc ctgggaaagg cctggaatgg gtttcagcta ttagtggtaa tggaggtagt     240
actcgttacg cagacagtgt gaaaggtcgc ttcaccatca gccgtgataa ttctaagaac     300
actttgtacc tgcaaatgaa ctccttgcgc gcagaagaca cggctgtgta ctattgtgcc     360
cgtgatcgct ttcggaaggt tcatggtttc gatgtatggg gacaaggtac cctggtaacg     420
gtttctagcg gaggtggtgg gagtggtgga ggcggctcgg gtggaggtgg ttcaggagga     480
ggcggagata tccaaatgac tcaatctcct agttcactgt cagcctctgt tggtgatcgc     540
gtgaccatta cctgccaagc tagccaggat attagcaact acttgaactg gtatcagcag     600
aagcctggca agcccccaaa gctgttgatc tacgatgcaa gtaacttgga aactggcgtc     660
ccaagccgct ctctggatc tggttcaggc accgacttca ctttcactat cagcagcctg     720
cagcctgaag atatcgcaac ctactattgc cagcaggatg ctactttttcc tttgactttc     780
ggccaaggca ccaaggtgga gatcaaggcg ccgcgctga gcaacagcat catgtacttc     840
agccacttcg tgcctgtgtt cctgcctgcc aagcctacaa caacaccagc cctagacct      900
ccaaccctg cccctacaat tgcctctcag cctctgtctc tgaggcccga agcttgtaga     960
cctgctgctg gcggagctgt gcacaccaga ggactggatt cgcctgcctt ttgggtgctg    1020
gtggtcgtgg gcggagtgct ggcttgttat tctctgctgg tcaccgtggc cttcatcatc    1080
ttttgggtcc gactgaagat ccaggtccga aaggccgcca tcaccagcta cgagaagtct    1140
gatggcgtgt acaccggcct gagcaccaga aaccaggaaa cctacgagac actgaagcac    1200
gagaagcccc cccag                                                     1215

<210> SEQ ID NO 3
<211> LENGTH: 41
<212> TYPE: PRT
<213> ORGANISM: Homo sapiens

<400> SEQUENCE: 3

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
            35                  40
```

```
<210> SEQ ID NO 4
<211> LENGTH: 123
<212> TYPE: DNA
<213> ORGANISM: Homo sapiens

<400> SEQUENCE: 4
ctgaagatcc aggtccgaaa ggccgccatc accagctacg agaagtctga tggcgtgtac      60
accggcctga gcaccagaaa ccaggaaacc tacgagacac tgaagcacga gaagccccc     120 cag                                                                   123

<210> SEQ ID NO 5
<211> LENGTH: 64
<212> TYPE: PRT
<213> ORGANISM: Homo sapiens

<400> SEQUENCE: 5

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

<210> SEQ ID NO 6
<211> LENGTH: 195
<212> TYPE: DNA
<213> ORGANISM: Homo sapiens

<400> SEQUENCE: 6
gcgctgagca acagcatcat gtacttcagc cacttcgtgc ctgtgttcct gcctgccaag      60
cctacaacaa caccagcccc tagacctcca acccctgccc ctacaattgc ctctcagcct     120
ctgtctctga ggcccgaagc ttgtagacct gctgctggcg gagctgtgca caccagagga     180
ctggatttcg cctgc                                                      195

<210> SEQ ID NO 7
<211> LENGTH: 28
<212> TYPE: PRT
<213> ORGANISM: Homo sapiens

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 8
<211> LENGTH: 84
<212> TYPE: DNA
<213> ORGANISM: Homo sapiens

<400> SEQUENCE: 8
ttttgggtgc tggtggtcgt gggcggagtg ctggcttgtt attctctgct ggtcaccgtg      60
gccttcatca tcttttgggt ccga                                             84

<210> SEQ ID NO 9
```

```
<211> LENGTH: 133
<212> TYPE: PRT
<213> ORGANISM: Artificial Sequence
<220> FEATURE:
<223> OTHER INFORMATION: CD8-CD28-FceRIgamma

<400> SEQUENCE: 9

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Phe Trp Val Leu Val Val Gly Gly Val Leu Ala Cys Tyr Ser Leu
65                  70                  75                  80

Leu Val Thr Val Ala Phe Ile Ile Phe Trp Val Arg Leu Lys Ile Gln
                85                  90                  95

Val Arg Lys Ala Ala Ile Thr Ser Tyr Glu Lys Ser Asp Gly Val Tyr
            100                 105                 110

Thr Gly Leu Ser Thr Arg Asn Gln Glu Thr Tyr Glu Thr Leu Lys His
        115                 120                 125

Glu Lys Pro Pro Gln
    130

<210> SEQ ID NO 10
<211> LENGTH: 399
<212> TYPE: DNA
<213> ORGANISM: Artificial Sequence
<220> FEATURE:
<223> OTHER INFORMATION: CD8-CD28-FceRIgamma (nucleic acid sequence)

<400> SEQUENCE: 10
ctgagcaaca gcatcatgta cttcagccac ttcgtgcctg tgttcctgcc tgccaagcct      60
acaacaacac cagcccctag acctccaacc cctgccccta caattgcctc tcagcctctg     120
tctctgaggc ccgaagcttg tagacctgct gctggcggag ctgtgcacac cagaggactg     180
gatttcgcct gcttttgggt gctggtggtc gtgggcggag tgctggcttg ttattctctg     240
ctggtcaccg tggccttcat catctttttgg gtccgactga agatccaggt ccgaaaggcc    300
gccatcacca gctacgagaa gtctgatggc gtgtacaccg gcctgagcac cagaaaccag     360
gaaacctacg agacactgaa gcacgagaag ccccccccag                           399

<210> SEQ ID NO 11
<211> LENGTH: 254
<212> TYPE: PRT
<213> ORGANISM: Homo sapiens

<400> SEQUENCE: 11

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60
```

```
Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 12
<211> LENGTH: 765
<212> TYPE: DNA
<213> ORGANISM: Homo sapiens

<400> SEQUENCE: 12

```
atgtggcagc tgctcctccc aactgctctg ctacttctag tttcagctgg catgcggact    60
gaagatctcc caaaggctgt ggtgttcctg agcctcaat  ggtacagggt gctcgagaag   120
gacagtgtga ctctgaagtg ccaggggagcc tactcccctg aggacaattc acacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagaccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg ggcttttgg gagtaaaaat    540
gtgtcttcag agactgtgaa catcaccatc actcaaggtt tggcagtgtc aaccatctca   600
tcattctttc cacctgggta ccaagtctct ttctgcttgg tgatggtact cctttttgca   660
gtggacacag actatatttt ctctgtgaag acaaacattc gaagctcaac aagagactgg   720
aaggaccata atttaaatg gagaaaggac cctcaagaca aatga                    765
```

<210> SEQ ID NO 13
<211> LENGTH: 236
<212> TYPE: PRT
<213> ORGANISM: Homo sapiens

<400> SEQUENCE: 13

Arg Thr Glu Asp Leu Pro Lys Ala Val Val Phe Leu Glu Pro Gln Trp

|  | 1 |  |  | 5 |  |  |  |  | 10 |  |  |  |  | 15 |  |
|---|---|---|---|---|---|---|---|---|---|---|---|---|---|---|---|

Tyr Arg Val Leu Glu Lys Asp Ser Val Thr Leu Lys Cys Gln Gly Ala
                20                  25                  30

Tyr Ser Pro Glu Asp Asn Ser Thr Gln Trp Phe His Asn Glu Ser Leu
            35                  40                  45

Ile Ser Ser Gln Ala Ser Ser Tyr Phe Ile Asp Ala Ala Thr Val Asp
        50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
        195                 200                 205

Phe Ser Val Lys Thr Asn Ile Arg Ser Ser Thr Arg Asp Trp Lys Asp
    210                 215                 220

His Lys Phe Lys Trp Arg Lys Asp Pro Gln Asp Lys
225                 230                 235

<210> SEQ ID NO 14
<211> LENGTH: 765
<212> TYPE: DNA
<213> ORGANISM: Homo sapiens

<400> SEQUENCE: 14

| atgtggcagc tgctgctgcc tacagctctc ctgctgctgg tgtccgccgg catgagaacc | 60 |
| gaggatctgc ctaaggccgt ggtgttcctg aaccccagt ggtacagagt gctggaaaag | 120 |
| gacagcgtga ccctgaagtg ccagggcgcc tacagcccg aggacaatag cacccagtgg | 180 |
| ttccacaacg agagcctgat cagcagccag gccagcagct acttcatcga cgccgccacc | 240 |
| gtggacgaca gcggcgagta tagatgccag accaacctga gcaccctgag cgaccccgtg | 300 |
| cagctggaag tgcacatcgg atggctgctg ctgcaggccc cagatgggt gttcaaagaa | 360 |
| gaggacccca tccacctgag atgccactct tggaagaaca ccgccctgca caaagtgacc | 420 |
| tacctgcaga acggcaaggg cagaaagtac ttccaccaca cagcgactt ctacatcccc | 480 |
| aaggccaccc tgaaggactc cggctcctac ttctgcagag gcctcgtggg cagcaagaac | 540 |
| gtgtccagcg agacagtgaa catcaccatc acccagggcc tggccgtgtc taccatcagc | 600 |
| agctttttcc caccggcta ccaggtgtcc ttctgcctcg tgatggtgct gctgttcgcc | 660 |
| gtggacaccg gcctgtactt cagcgtgaaa acaaacatca gaagcagcac ccgggactgg | 720 |
| aaggaccaca gttcaagtg gcggaaggac ccccaggaca gtga | 765 |

<210> SEQ ID NO 15
<211> LENGTH: 41
<212> TYPE: PRT
<213> ORGANISM: Homo sapiens

<400> SEQUENCE: 15

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40

<210> SEQ ID NO 16
<211> LENGTH: 123
<212> TYPE: DNA
<213> ORGANISM: Homo sapiens

<400> SEQUENCE: 16
ctgaagatcc aggtccgaaa ggccgccatc accagctacg agaagtctga tggcgtgtac      60
accggcctga gcaccagaaa ccaggaaacc tacgagacac tgaagcacga aagcccccc     120 cag                                                                  123

<210> SEQ ID NO 17
<211> LENGTH: 113
<212> TYPE: PRT
<213> ORGANISM: Homo sapiens

<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 18
<211> LENGTH: 339
<212> TYPE: DNA
<213> ORGANISM: Homo sapiens

<400> SEQUENCE: 18
gtgaagttca gcaggagcgc agacgccccc gcgtaccagc agggccagaa ccagctctat      60
aacgagctca tctaggacg aagagaggag tacgatgttt tggacaagag acgtggccgg     120
gaccctgaga tgggggaaa gccgcagaga aggaagaacc ctcaggaagg cctgtacaat     180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                        339

<210> SEQ ID NO 19
<211> LENGTH: 28
<212> TYPE: PRT
<213> ORGANISM: Homo sapiens

<400> SEQUENCE: 19

Phe Trp Val Leu Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 20
<211> LENGTH: 84
<212> TYPE: DNA
<213> ORGANISM: Homo sapiens

<400> SEQUENCE: 20
ttttgggtgc tggtggtcgt gggcggagtg ctggcttgtt attctctgct ggtcaccgtg      60
gccttcatca tcttttgggt ccga                                             84

<210> SEQ ID NO 21
<211> LENGTH: 250
<212> TYPE: PRT
<213> ORGANISM: Artificial Sequence
<220> FEATURE:
<223> OTHER INFORMATION: anti-B7-H4 scFv portion

<400> SEQUENCE: 21

Ala Gln Pro Ala Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Asn Ser Tyr Ala Met His Trp Val Arg Gln Ala Pro Gly Lys Gly
        35                  40                  45

Leu Glu Trp Val Ser Ala Ile Ser Gly Asn Gly Gly Ser Thr Arg Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg Asp Arg Phe Arg Lys Val His Gly Phe Asp
            100                 105                 110

Val Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Ser Asn Tyr Leu
                165                 170                 175

Asn Trp Tyr Gln Gln Lys Pro Gly Lys Ala Pro Lys Leu Leu Ile Tyr
            180                 185                 190

Asp Ala Ser Asn Leu Glu Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Asp Ala Thr Phe Pro Leu Thr
225                 230                 235                 240

Phe Gly Gln Gly Thr Lys Val Glu Ile Lys
                245                 250

<210> SEQ ID NO 22
<211> LENGTH: 738
<212> TYPE: DNA
<213> ORGANISM: Artificial Sequence
<220> FEATURE:
<223> OTHER INFORMATION: anti-B7-H4 scFv portion

<400> SEQUENCE: 22

```
gaagttcagc ttgtagaatc tggaggtgga ttggttcaac ctggtggctc tcttcgcctg      60
agttgtgcag cctctggttt tactttcaat agttacgcta tgcattgggt tcgtcaggct     120
cctgggaaag gcctggaatg ggtttcagct attagtggta atggaggtag tactcgttac     180
gcagacagtg tgaaaggtcg cttcaccatc agccgtgata attctaagaa cactttgtac     240
ctgcaaatga actccttgcg cgcagaagac acggctgtgt actattgtgc ccgtgatcgc     300
tttcggaagg ttcatggttt cgatgtatgg ggacaaggta ccctggtaac ggtttctagc     360
ggaggtggtg ggagtggtgg aggcggctcg ggtggaggtg gttcaggagg aggcggagat     420
atccaaatga ctcaatctcc tagttcactg tcagcctctg ttggtgatcg cgtgaccatt     480
acctgccaag ctagccagga tattagcaac tacttgaact ggtatcagca gaagcctggc     540
aaagccccaa agctgttgat ctacgatgca agtaacttgg aaactggcgt cccaagccgc     600
ttctctggat ctggttcagg caccgacttc actttcacta tcagcagcct gcagcctgaa     660
gatatcgcaa cctactattg ccagcaggat gctacttttc ctttgacttt cggccaaggc     720
accaaggtgg agatcaag                                                   738
```

<210> SEQ ID NO 23
<211> LENGTH: 153
<212> TYPE: PRT
<213> ORGANISM: Homo sapiens

<400> SEQUENCE: 23

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr

<210> SEQ ID NO 24
<211> LENGTH: 459
<212> TYPE: DNA
<213> ORGANISM: Homo sapiens

<400> SEQUENCE: 24

```
atgtaccgga tgcagctgct gagctgtatc gccctgtctc tggccctcgt gaccaacagc    60
gcccctacca gcagcagcac caagaaaacc cagctgcagc tggaacatct gctgctggac   120
ctgcagatga tcctgaacgg catcaacaac tacaagaacc ccaagctgac ccggatgctg   180
accttcaagt tctacatgcc caagaaggcc accgaactga acatctgca gtgcctggaa    240
gaggaactga agcccctgga agaagtgctg aacctggccc agagcaagaa cttccacctg   300
aggcccaggg acctgatcag caacatcaac gtgatcgtgc tggaactgaa aggcagcgag   360
acaaccttca gtgcgagta cgccgacgag acagctacca tcgtggaatt tctgaaccgg   420
tggatcacct tctgccagag catcatcagc accctgacc               459
```

<210> SEQ ID NO 25
<211> LENGTH: 160
<212> TYPE: PRT
<213> ORGANISM: Artificial Sequence
<220> FEATURE:
<223> OTHER INFORMATION: erIL-2

<400> SEQUENCE: 25

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160
```

<210> SEQ ID NO 26
<211> LENGTH: 480
<212> TYPE: DNA
<213> ORGANISM: Artificial Sequence
<220> FEATURE:
<223> OTHER INFORMATION: erIL-2 (nucleic acid sequence)

<400> SEQUENCE: 26

```
atgtaccgga tgcagctgct gagctgtatc gccctgtctc tggccctcgt gaccaacagc    60
gcccctacca gcagcagcac caagaaaacc cagctgcagc tggaacatct gctgctggac   120
```

```
ctgcagatga tcctgaacgg catcaacaac tacaagaacc ccaagctgac ccggatgctg    180
accttcaagt tctacatgcc caagaaggcc accgaactga acatctgca gtgcctggaa    240 gaggaactga agccctgga agaagtgctg aacctggccc agagcaagaa cttccacctg    300
aggcccaggg acctgatcag caacatcaac gtgatcgtgc tggaactgaa aggcagcgag    360
acaaccttca tgtgcgagta cgccgacgag acagctacca tcgtggaatt tctgaaccgg    420
tggatcacct tctgccagag catcatcagc accctgaccg ctccgagaa ggacgagctg    480
```

```
<210> SEQ ID NO 27
<211> LENGTH: 169
<212> TYPE: PRT
<213> ORGANISM: Artificial Sequence
<220> FEATURE:
<223> OTHER INFORMATION: erIL-15

<400> SEQUENCE: 27

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Ser Glu Lys Asp Glu Leu
                165
```

```
<210> SEQ ID NO 28
<211> LENGTH: 510
<212> TYPE: DNA
<213> ORGANISM: Artificial Sequence
<220> FEATURE:
<223> OTHER INFORMATION: erIL-15 (nucleic acid sequence)

<400> SEQUENCE: 28
atgcgcatca gcaagcccca cctgcgcagc atcagcatcc agtgctacct gtgcctgctg     60
ctgaacagcc acttcctgac cgaggccggc atccacgtgt tcatcctggg ctgcttcagc    120
gccggcctgc ccaagaccga ggccaactgg gtgaacgtga tcagcgacct gaagaagatc    180
gaggacctga tccagagcat gcacatcgac gccaccctgt acaccgagag cgacgtgcac    240
cccagctgca aggtgaccgc catgaagtgc ttcctgctgg agctgcaggt gatcagcctg    300
gagagcggcg acgccagcat ccacgacacc gtggagaacc tgatcatcct ggccaacaac    360
agcctgagca gcaacggcaa cgtgaccgag agcggctgca aggagtgcga ggagctggag    420
```

```
gagaagaaca tcaaggagtt cctgcagagc ttcgtgcaca tcgtgcagat gttcatcaac    480
accagcggct ccgagaagga cgagctgtaa                                      510

<210> SEQ ID NO 29
<211> LENGTH: 1437
<212> TYPE: DNA
<213> ORGANISM: Artificial Sequence
<220> FEATURE:
<223> OTHER INFORMATION: 1st generation CAR with CD3 zeta signaling
      domain

<400> SEQUENCE: 29
atggactgga tctggcggat tctgtttctc gtgggagctg ccacaggcgc tcattctgct     60
cagcctgccg atatccagat gacccagaca acaagcagcc tgagcgcctc tctgggcgat   120
agagtgacaa tcagctgcag agccagccag gacatcagca agtacctgaa ctggtatcag   180
cagaaacccg acggcaccgt gaagctgctg atctaccaca caagcagact gcacagcggc   240
gtgccaagca gattttctgg cagcggcagc ggcaccgatt acagcctgac catcagcaac   300
ctggaacagg aagatatcgc tacctacttc tgtcagcagg gcaacaccct gccttacacc   360
tttggcggcg gaacaaagct ggaactgaaa agaggcggcg aggaagcgg aggcggagga   420 tctggggcg gaggctctgg cggaggggga tctgaagtgc agctgcagca gtctggacct   480
ggactggtgg ctccttctca gtccctgtct gtgacctgta cagtgtctgg cgtgtccctg   540
cctgattacg gcgtgtcctg gatcagacag cctcccagaa aaggcctgga atggctggga   600
gtgatctggg gcagcgagac aacctactac aacagcgccc tgaagtcccg gctgaccatc   660
atcaaggaca cagcaagag ccaggtgttc ctgaagatga acagcctgca gaccgacgac   720
accgccatct actactgcgc caagcactac tactacggcg gcagctacgc catggattat   780
tggggccagg gcaccaccgt gacagtgtca tctgcggccg cgctgagcaa cagcatcatg   840
tacttcagcc acttcgtgcc tgtgttcctg cctgccaagc ctacaacaac accagccccct   900 agacctccaa cccctgcccc tacaattgcc tctcagcctc tgtctctgag gcccgaagct   960
tgtagacctg ctgctggcgg agctgtgcac accagaggac tggatttcgc ctgcttttgg  1020
gtgctggtgg tcgtgggcgg agtgctggct tgttattctc tgctggtcac cgtggccttc  1080
atcatctttt gggtccgagt gaagttcagc agatccgccg atgcccctgc ttaccagcag  1140
ggccagaatc agctgtacaa cgagctgaac ctgggcagac gggaagagta cgacgtgctg  1200
gataagagaa gaggcagaga tcccgagatg ggcggcaagc cccagagaag aaagaatccc  1260
caggaaggcc tgtataacga actgcagaaa gacaagatgg ccgaggccta cagcgagatc  1320
ggcatgaagg gcgagagaag aagaggcaag ggccacgatg gactgtacca gggactgagc  1380
acagccacca aggatacccta cgatgccctg cacatgcagg ccctgcctcc aagataa    1437

<210> SEQ ID NO 30
<211> LENGTH: 1221
<212> TYPE: DNA
<213> ORGANISM: Artificial Sequence
<220> FEATURE:
<223> OTHER INFORMATION: 1st generation CAR with a FceRIgamma signaling
      domain

<400> SEQUENCE: 30
atggactgga tctggcggat tctgtttctc gtgggagctg ccacaggcgc tcattctgct     60
cagcctgccg atatccagat gacccagaca acaagcagcc tgagcgcctc tctgggcgat   120
```

```
agagtgacaa tcagctgcag agccagccag gacatcagca agtacctgaa ctggtatcag    180
cagaaacccg acggcaccgt gaagctgctg atctaccaca caagcagact gcacagcggc    240
gtgccaagca gattttctgg cagcggcagc ggcaccgatt acagcctgac catcagcaac    300
ctggaacagg aagatatcgc tacctacttc tgtcagcagg gcaacaccct gccttacacc    360
tttggcggcg gaacaaagct ggaactgaaa agaggcggcg gaggaagcgg aggcggagga    420 tctggggcg gaggctctgg cggaggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca acagcaagag ccaggtgttc ctgaagatga cagcctgca gaccgacgac    720 accgccatct actactgcgc caagcactac tactacggcg gcagctacgc catggattat    780
tggggccagg gcaccaccgt gacagtgtca tctgcggccg cgctgagcaa cagcatcatg    840
tacttcagcc acttcgtgcc tgtgttcctg cctgccaagc ctacaacaac accagcccct    900
agacctccaa ccccctgccc tacaattgcc tctcagcctc tgtctctgag gcccgaagct    960
tgtagacctg ctgctggcgg agctgtgcac accagaggac tggatttcgc ctgcttttgg   1020
gtgctggtgg tcgtgggcgg agtgctggct tgttattctc tgctggtcac cgtggccttc   1080
atcatctttt gggtccgact gaagatccag gtccgaaagg ccgccatcac cagctacgag   1140
aagtctgatg gcgtgtacac cggcctgagc accagaaacc aggaaaccta cgagacactg   1200
aagcacgaga agccccccca g                                             1221
```

ANTI-B7-H4 CHIMERIC ANTIGEN RECEPTOR-MODIFIED NK-92 CELLS

SEQUENCE LISTING

The content of the ASCII text file of the sequence listing named 104077.0012PCT_ST25, which is 33 kb in size was created on 7/24/19 and electronically submitted via EFS-Web along with the present application is incorporated by reference in its entirety.

FIELD OF THE INVENTION

The field of the invention is recombinant nucleic acids and cells containing same to generate genetically modified cells that express a chimeric antigen receptor (CAR), and in particular modified NK and NK-92 cells expressing an anti-B7-H4 CAR having an Fc epsilon receptor gamma (FcεRIγ) signaling domain.

BACKGROUND OF THE INVENTION

Natural killer (NK) cells are increasingly used in immune therapy and are known to kill a variety of cells, including virus-infected cells and many malignant cells. Notably, NK cell killing is in most cases non-specific with regard to a particular antigen. Moreover, NK activity does not require prior immune sensitization and is typically mediated by cytolytic proteins, including perforin, granzyme, and granulysin. To increase the potential usefulness of these cells, NK cells can be modified with targeting molecules, and especially chimeric antigen receptors.

Notably, the first generation of CARs was used in T-cells and contained only a single cytoplasmic signaling domain. For example, one version of a first-generation CAR in T-cells included a signaling domain from the Fc epsilon receptor gamma (FcεRIγ) which contained one immunoreceptor tyrosine-based activation motif (ITAM). Another version contained the signaling domain from CD3ζ which contained three ITAMs. In vivo and in vitro studies have shown that the CD3ζ CAR T-cells were more efficient at tumor eradication than FcεRIγ CAR T-cells (e.g., Haynes, et al. 2001, *J. Immunology* 166:182-187; Cartellieri, et al. 2010, *J. Biomed and Biotech*, Vol. 2010, Article ID 956304).

Further studies then revealed that certain costimulatory signals were required for full activation and proliferation of such recombinant T-cells, and second and third generation CARs combined multiple signaling domains in to a single CAR to enhance efficacy of the recombinant CAR T-cells. Due to their less desirable philological effects in the tested T-cells, first generation CARs and the FcεRIγ signaling domains were largely discarded in favor of the new, more efficient CARs using CD3ζ in combination with one or more added signaling domains (e.g., Hermanson and Kaufman 2015, *Frontiers in Immunol.*, Vol. 6, Article 195).

More recently, selected CARs have also been expressed in NK cells. For example, CAR-modified NK-92 cells have used first generation CARs with only a CD3ζ intracellular signaling domain. Several antigens have been targeted by these first generation CAR-NK cells, including CD19 and CD20 for B cell lymphoma, ErbB2 for breast, ovarian, and squamous cell carcinoma, GD2 for neuroblastoma, and CD138 for multiple myeloma. Second generation CAR-NK cells from the NK-92 line have also been created for several antigens, including EpCAM for multiple carcinomas HLA-A2 EBNA3 complex for Epstein-Barr virus, CS1 for multiple myeloma, and ErbB2 for HER2 positive epithelial cancers. The most common intracellular costimulatory domain used alongside CD3ζ in second generation NK-92 CARs is CD28. However, the potential effect of the CD28 domain is unclear since NK cells do not naturally express CD28. Additional second generation CARs have incorporated the 4-1BB intracellular signaling domain along with CD3ζ to improve NK cell persistence. Others compared functionality of different intracellular domains using an ErbB2 scFv fused with CD3ζ alone, CD28 and CD3ζ, or 4-1BB and CD3ζ tested against breast cancer cells. They found that both of the second generation constructs improved killing compared to the first generation CARs and the CD28 and CD3ζ had 65% target lysis, the 4-1BB and CD3ζ lysed 62%, and CD3ζ alone killed 51% of targets. 4-1BB and CD28 intracellular domains were also compared in a recent study using anti-CD19 CARs expressed on NK-92 cells for B cell malignances. Still others found that CD3ζ/4-1BB constructs were less effective than CD3ζ/CD28 in cell killing and cytokine production, highlighting differential effects of CD28 and 4-1BB costimulatory domains.

Third generation NK-92 CARs were constructed of an anti-CD5 scFv with CD3ζ, CD28, and 4-1BB intracellular signaling domains and demonstrated specific and potent anti-tumor activity against a variety of T-cell leukemia and lymphoma cell lines and primary tumor cells. Such cells were also able to inhibit disease progression in xenograft mouse models of T cell Acute lymphoblastic leukemia (ALL) cell lines as well as primary tumor cells (*Transl Res.* 2017 September; 187: 32-43). In further examples, WO 2016/201304 and WO 2018/076391 teach use of third generation CD3ζ CARs expressed in NK cells and NK-92 cells. Likewise, US 2016/0361360 teaches third generation CAR constructs for use in T and NK cells in which the intracellular portion contained a CD28 segment, a 4-1BB segment, and a CD3ζ segment.

While use of CARs to target NK cells to a specific molecule is at least conceptually relatively simple numerous difficulties nevertheless remain. For example, expression levels of CARs are often low. Moreover, the duration of expression the CAR over time is in many cases less than desirable. In addition, autologous NK cells/NK-92 cells require exogenous IL-2 as a survival factor and enhancer of cytotoxic potential. Unfortunately, systemic administration of IL-2 is often associated with significant undesirable side effects and toxicity. To overcome such issues, the cells can be cultivated and expanded in vitro prior to administration to a patient. While IL-2 will allow generation of sufficient quantities of NK cells or NK-92 cells, use of exogenous IL-2 in large scale production of NK cells is typically cost-prohibitive. The requirement for exogenous IL-2 was resolved, for example, by recombinant expression of IL-2 confined to the endoplasmic reticulum from a retroviral vector (see *Exp Hematol.* 2005 February; 33(2):159-64). Such approach eliminated the requirement for exogenous IL-2. However, retroviral transfection efficiency is often less than desirable and will be even more inefficient where multiple recombinant genes are to be expressed.

Furthermore, NK cells and particularly NK-92 cells are often difficult to genetically modify as evidenced by numerous failures to engineer NK-92 cells to express an Fc receptor. Such difficulties are further compounded where NK-92 cells are transfected with multiple recombinant genes or relatively large recombinant nucleic acid payload for heterologous expression. Additionally, NK-92 cells also exhibit a significant lack of predictability with respect to recombinant expression of exogenous proteins (e.g., CD16).

On a functional level, most if not all CAR NK-92 cells require a relatively high effector to target cell ratio, likely due to relatively low expression of the CAR construct. Moreover, such CAR NK-92 cells will also experience a fast decline in cytotoxicity over time, thus rendering such cells clinically less attractive.

Therefore, even though numerous recombinant NK-92 cells are known in the art, all or almost all of them suffer from various difficulties. Consequently, there remains a need for CAR-expressing NK-92 cells that express a high-activity CAR (and especially an anti-B7-H4 CAR) in significant quantities with attendant persistent cytotoxicity, and that allow for easy cultivation in a simple and effective manner.

SUMMARY OF THE INVENTION

The inventors have discovered that anti-B7-H4 NK-92 cells can be efficiently made by transfection with a recombinant nucleic acid that encodes an FcεRIγ-containing anti-B7-H4 CAR. Notably, CARs with a FcεRIγ signaling domain significantly increased expression levels of the CAR and further conveyed extended cytotoxicity over time. Contemplated recombinant nucleic acids that encode the anti-B7-H4 CAR are preferably in a tricistronic arrangement that also includes a sequence portion that encodes CD16 or CD16 variant, and/or IL-2 (or IL-15) or an IL-2 (or IL-15) variant. Advantageously, such recombinant nucleic acids not only provide an efficient manner of selecting transfected cells (as the IL-2 not only imparts autocrine growth stimulation but also acts as a selection marker for the co-expressed proteins), but also yield CAR NK cells with superior cytolytic activity (e.g., at a relatively low effector to target cell ratio as compared to other constructs) and high levels of expression of the CD16 and the FcεRIγ-containing CAR.

In one aspect of the inventive subject matter, the inventors contemplate a genetically modified anti-B7-H4 CAR NK cell that comprises a recombinantly expressed cytokine, a recombinantly expressed CD16, and a membrane bound recombinantly expressed anti-B7-H4 chimeric antigen receptor (CAR) that comprises in a single polypeptide chain an extracellular binding domain, a hinge domain, a transmembrane domain, and a FcεRIγ signaling domain. Among other options the NK cell may be an NK-92 cell.

In some embodiments, the recombinantly expressed cytokine comprises IL-2 or IL-15, and/or the recombinantly expressed cytokine may comprise an endoplasmic retention sequence. Where desired, the recombinantly expressed CD16 may be a high-affinity CD16 variant having a 158V mutation, and/or the extracellular binding domain of the CAR comprises a scFv.

In further embodiments, the recombinantly expressed cytokine, the recombinantly expressed CD16, and the recombinantly expressed CAR are expressed from a tricistronic recombinant nucleic acid, or the recombinantly expressed cytokine and/or the recombinantly expressed CD16 is expressed from a recombinant nucleic acid that is integrated into the genome of the NK cell. In other embodiments, the anti-B7-H4 CAR has an amino acid sequence of SEQ ID NO:1, which is encoded by the nucleic acid having a sequence of SEQ ID NO:2.

Therefore, and viewed from a different perspective, the inventors also contemplate a recombinant nucleic acid that includes a first sequence portion encoding a cytokine, a second sequence portion encoding a CD16, and a third sequence portion encoding an anti-B7-H4 CAR that comprises in a single polypeptide chain an extracellular binding domain, a hinge domain, a transmembrane domain, and a FcεRIγ signaling domain. Most typically, the first, the second, and the third sequence portions are on the same nucleic acid.

For example, contemplated recombinant nucleic acids may be a tricistronic RNA or a tricistronic DNA. In further examples, the cytokine is IL-2 or IL15, and where desired, the cytokine may also comprise an endoplasmic retention sequence. In other examples, the CD16 is a high-affinity CD16 variant may have a 158V mutation, and/or the extracellular binding domain comprises a scFv. In still further contemplated examples, the hinge domain and/or the transmembrane domain comprise a CD8 hinge domain and/or a CD28 transmembrane domain. Therefore, a contemplated anti-B7-H4 CAR may have an amino acid sequence of SEQ ID NO:1, which is encoded by the nucleic acid having a sequence of SEQ ID NO:2.

In yet further contemplated aspects, the inventors contemplate various recombinant cells that comprise the recombinant nucleic acid presented herein. For example, suitable cells include bacterial cells and autologous NK cells (relative to an individual receiving the recombinant cell). Of course, it should also be recognized that the NK cell may be an NK-92 cell that is optionally genetically modified.

Therefore, the inventors also contemplate a method of treating cancer in a patient in need thereof, where such method includes a step of administering to the patient a therapeutically effective amount of any the genetically modified NK cells presented herein to thereby treat the cancer. In such methods, at least one additional therapeutic entity may be administered, such as a viral cancer vaccine, a bacterial cancer vaccine, a yeast cancer vaccine, N-803, a bi-specific engager, an antibody, a stem cell transplant, and/or a tumor targeted cytokine. Moreover, suitable additional therapeutic agents include NK cells, and especially primary NK cells.

Contemplated cancers treatable by such methods include leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Various objects, features, aspects and advantages of the inventive subject matter will become more apparent from the following detailed description of preferred embodiments along with the accompanying drawing figures in which like numerals represent like components.

DETAILED DESCRIPTION OF THE INVENTION

Figure 1:
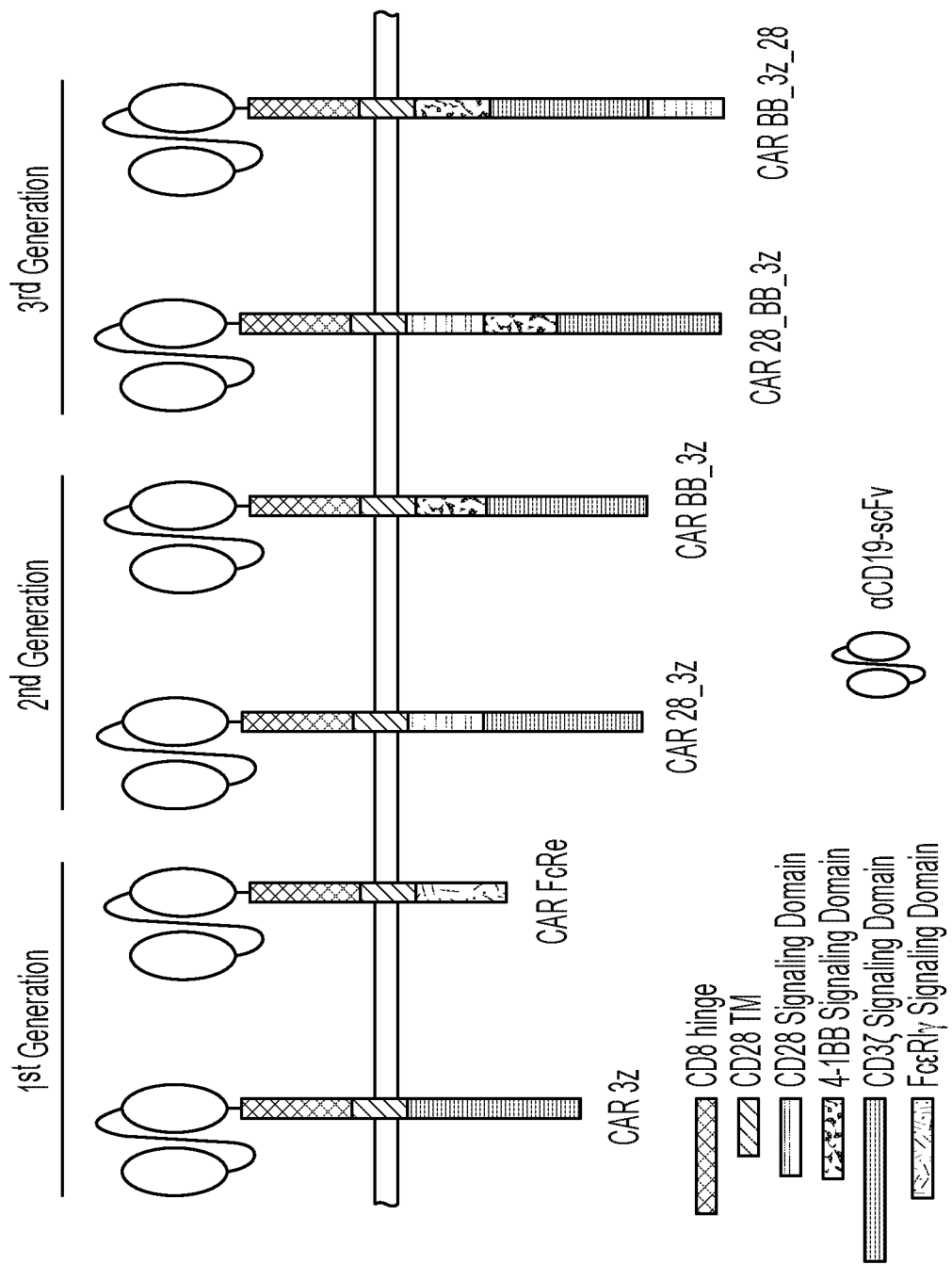
FIG. 1 is a schematic representation of exemplary CARs variants. All of the CAR variants contained an extracellular domain comprising a representative exemplary scFv region (anti-CD19 scFv; αCD19-scFv), a hinge region from CD8 (CD8 hinge), and a transmembrane domain from CD28 (CD28 TM). The specific intracellular domains of the CARs were as indicated.

The inventors have discovered highly active genetically modified NK cells expressing an anti-B7-H4 CAR. Most notably, CAR mediated cytotoxicity, ADCC, and CAR expression in recombinant NK cells (e.g. NK-92 cells) were substantially higher where the recombinant CAR included an FcεRIγ signaling domain as is described in more detail below. In this context, it must be recognized that the finding that a CAR with an FcεRIγ signaling domain has superior properties in NK cells is especially unexpected as such CARs when expressed in T cells have performed relatively poorly as compared to CARs that had a CD3ζ, a 4-1BB, or a CD28 signaling domain and optionally additional signaling domains as commonly found in second and third generation CARs.

Therefore, in some embodiments recombinant nucleic acids are contemplated that encode an anti-B7-H4 CAR with an FcεRIγ signaling domain, preferably but not necessarily in a tricistronic arrangement that also includes a sequence portion that encodes CD16 or a CD16 variant, and/or IL-2 or an IL-2 variant. In still further advantageous aspects of the inventive subject matter, such recombinant nucleic acid will not only provide an efficient manner of selecting transfected cells (as IL-2 not only imparts autocrine growth stimulation but also acts as a selection marker for the co-expressed proteins). Of course, it should be appreciated that the IL-2 or IL-2 variant may be replaced with IL-15 or an IL-15 variant.

Consequently, the inventive subject matter is directed to genetically modified NK cells, NK-92 cells, and derivatives thereof that express a chimeric antigen receptor (CAR) on the cell surface where the anti-B7-H4 CAR preferably comprises an intracellular signaling domain from the Fc epsilon receptor gamma (FcεRIγ). For example, the cytoplasmic (intracellular) signaling domain of FcεRIγ may have an amino acid sequence having at least 95% sequence identity to SEQ ID NO:3, or comprises, consists of, or essentially consists of an amino acid sequence having the sequence as noted in SEQ ID NO:3. In some embodiments, the cytoplasmic signaling domain of FcεRIγ is encoded by a nucleic acid having at least 95% sequence identity to SEQ ID NO:4. Contemplated recombinant cells may further express various other proteins, including one or more cytokines and CD16. As will be readily appreciated, the CAR and/or other proteins may be transiently expressed by the recombinant cell, or stably expressed.

In some embodiments, the CAR comprises a hinge region from CD8 (having an amino acid sequence of SEQ ID NO:5, which is encoded by nucleic acid having SEQ ID NO: 6) and/or in some embodiments, the CAR comprises a transmembrane domain from CD28 (having an amino acid sequence of SEQ ID NO:7, which is encoded by nucleic acid having SEQ ID NO: 8). In further embodiments, a recombinant cell is genetically modified with a nucleic acid having a sequence that encodes a hybrid protein having a sequence of SEQ ID NO:9 (encoded by a nucleic acid having a sequence of SEQ ID NO: 10) comprising a CD8 hinge region that is coupled to a CD28 transmembrane domain that is coupled to an FcεRIγ signaling domain. As will be appreciated, addition of a binding domain to the hinge region of that hybrid protein will form a functional CAR, preferably with a binding domain that binds B7-H4.

In some embodiments, the nucleic acid construct further comprises a (inducible) promoter that promotes transcription of the nucleic acid sequences. Preferably, but not necessarily, the nucleic acid construct is a multi-cistronic vector or RNA comprising one or more Internal Ribosome Entry Site (IRES) to allow for initiation of translation from an internal region of an mRNA transcribed from the nucleic acid sequences. Alternatively, or additionally, the nucleic acid construct comprises a sequence that encodes a 2A peptide, such as a T2A, P2A, E2A, or F2A peptide, in order to produce equimolar levels of polypeptides encoded by the same mRNA. In some embodiments, the nucleic acid construct further comprises a nucleic acid sequence that encodes an antigen binding protein (ABP). In some embodiments, the ABP is an scFv or a codon optimized scFv that binds to B7-H4 with a $K_D$ of equal or less than $10^{-6}$ M, or equal or less than $10^{-7}$ M, or equal or less than $10^{-8}$ M, or equal or less than $10^{-9}$ M. In further embodiments, the construct comprises a nucleic acid that encodes a cytokine, such IL-2 or IL-15, which may be targeted to the endoplasmic reticulum. In some embodiments, the NK-92 cell or cell line is also genetically modified to express CD16 on the cell surface. In one embodiment, the NK-92 cell or cell line is genetically modified to express a high affinity CD16 (F158V) on the cell surface.

With respect to suitable NK cells, it should be noted that all NK cells are deemed suitable for use herein and therefore include primary NK cells (preserved, expanded, and/or fresh cells), secondary NK cells that have been immortalized, autologous or heterologous NK cells (banked, preserved, fresh, etc.), and modified NK cells as described in more detail below. In some embodiments, it is preferred that the NK cells are NK-92 cells. The NK-92 cell line is a unique cell line that was discovered to proliferate in the presence of interleukin 2 (IL-2) (see e.g., Gong et al., *Leukemia* 8:652-658 (1994)). NK-92 cells are tumor derived NK cells with broad anti-tumor cytotoxicity and predictable yield after expansion in suitable culture media. Advantageously, NK-92 cells have high cytolytic activity against a variety of cancers.

The original NK-92 cell line expressed the CD56bright, CD2, CD7, CD11a, CD28, CD45, and CD54 surface markers and did not display the CD1, CD3, CD4, CD5, CD8, CD10, CD14, CD16, CD19, CD20, CD23, and CD34 markers. Growth of such NK-92 cells in culture is dependent upon the presence of interleukin 2 (e.g., rIL-2), with a dose as low as 1 IU/mL being sufficient to maintain proliferation. IL-7 and IL-12 do not support long-term growth, nor have various other cytokines tested, including IL-1$\alpha$, IL-6, tumor necrosis factor $\alpha$, interferon $\alpha$, and interferon $\gamma$. Compared to primary NK cells, NK-92 typically have a high cytotoxicity even at relatively low effector:target (E:T) ratios, e.g. 1:1. Representative NK-92 cells are deposited with the American Type Culture Collection (ATCC), designation CRL-2407.

Therefore, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.), or that certain NK cells may be naturally devoid of various KIRs. Most typically, more than one KIR will be mutated, deleted, not expressed, or silenced, and especially contemplated KIR include those with two or three domains, with short or long cytoplasmic tail. Viewed from a different perspective, modified, silenced, not expressed or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and/or KIR3DS1. Such modified cells may be prepared using protocols well known in the art. Alternatively, such cells may also be commercially obtained from NantKwest as aNK cells. Such cells may then be additionally genetically modified to a CAR as further described in more detail below.

In another aspect of the inventive subject matter, the genetically engineered NK cell may also be an NK-92 derivative that is modified to express the high-affinity Fc$\gamma$ receptor (CD16). Sequences for high-affinity variants of the Fc$\gamma$ receptor are well known in the art (see e.g., *Blood* 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fc$\gamma$ receptor). Alternatively, such cells may also be commercially obtained from NantKwest as haNK cells. Such cells may then be additionally genetically modified to a CAR as further described in more detail below.

Genetic modification of the NK cells contemplated herein can be performed in numerous manners, and all known manners are deemed suitable for use hereon. Moreover, it should be recognized that NK cells can be transfected with DNA or RNA, and the particular choice of transfection will at least in part depend on the type of desired recombinant cell and transfection efficiency. For example, where it is desired that NK cells are stably transfected, linearized DNA may be introduced into the cells for integration into the genome. On the other hand, where transient transfection is desired, circular DNA or linear RNA (e.g., mRNA with polyA+tail) may be used.

For example, where the NK cell is an autologous NK cell or an NK-92 cell it is contemplated that the recombinant nucleic acid will include a segment that encodes a CAR that includes Fc$\varepsilon$RI$\gamma$ signaling domain, and preferably also a segment that encodes a cytokine to provide autocrine growth stimulation (e.g., IL-2, IL-2 that is modified with an ER retention sequence, IL-15, or IL-15 that is modified with an ER retention sequence) and/or a segment that encodes a CD16 or high affinity CD16$^{158V}$. As will be readily appreciated, inclusion of a cytokine that provides autocrine growth stimulation will render the modified recombinant independent of exogenous cytokine addition, which will render large scale production of such cells economically feasible. Likewise, where the modified recombinant also expresses CD16 or a high affinity CD16$^{158V}$, such cells will have further enhanced ADCC characteristics and with that further improved targeted cytotoxicity.

Of course, it should be recognized that the recombinant nucleic acid that encodes that cytokine and/or the CD16 or high affinity CD16$^{158V}$ can be integrated in to the genome of the NK cell, or can be supplied as an extrachromosomal unit (which may be a linear or circular DNA, or a linear RNA, virally delivered or via chemical, mechanical, or electrical transfection). For example, recombinant NK-92 cells expressing IL-2ER and CD16158V are known as haNK cells (*Oncotarget* 2016 Dec. 27; 7(52): 86359-86373) and can be transfected with a recombinant nucleic acid that includes a segment that encodes a CAR that includes Fc$\varepsilon$RI$\gamma$ signaling domain. Once more, such recombinant nucleic acid may comprise further segments that may encode additional immunotherapeutic proteins, such as N-803, TxM-type compounds, IL-8 traps, TGF-$\beta$ traps, etc. Likewise, NK-92 cells may already be transfected with a cDNA that encodes IL-2 (e.g., NK-92MI, ATCC CRL-2408). Such cells can then be further transfected with a recombinant nucleic acid that includes a segment that encodes a CAR that includes Fc$\varepsilon$RI$\gamma$ signaling domain along with a segment that encodes a CD16 or high affinity CD16$^{158V}$.

On the other hand, (autologous, fresh, cultivated, or previously frozen) NK cells or NK-92 cells may also be transfected with a recombinant nucleic acid that includes a segment that encodes a CAR with a Fc$\varepsilon$RI$\gamma$ signaling domain, a segment that encodes a cytokine to provide autocrine growth stimulation (e.g., IL-2, IL-2 that is modified with an ER retention sequence, IL-15, or IL-15 that is modified with an ER retention sequence) and a segment that encodes a CD16 polypeptide (having an amino acid sequence of SEQ ID NO: 11, which is encoded by nucleic acid having SEQ ID NO: 12) or a high affinity CD16$^{158V}$ polypeptide (having an amino acid sequence of SEQ ID NO: 13, which is encoded by nucleic acid having SEQ ID NO: 14). Most typically, such recombinant nucleic acid will be arranged as a tricistronic construct. As noted before, such constructed can be an extrachromosomal circular plasmid, a linear DNA (which may be integrated into the genome of the NK cell), or a linear RNA. Such nucleic acids will typically be transfected into the cells in a manner well known in the art (e.g., electroporation, lipofection, ballistic gene transfer, etc.). Similarly, the nucleic acid may be delivered to the cell via a recombinant virus. Therefore, NK cells suitable for use herein include NK-92 cells (which may be transfected with a tricistronic construct encoding a CAR, a CD16 or variant thereof, and a cytokine or variant thereof), a genetically modified NK cell or NK-92 cell that expresses a CD16 or variant thereof or a cytokine or variant thereof (which may be transfected with a nucleic acid encoding a CAR and a CD16 or variant thereof or a cytokine or variant thereof), and a genetically modified NK cell or NK-92 cell that expresses a CD16 or variant thereof and a cytokine or variant thereof (which may be transfected with a nucleic acid encoding a CAR).

In preferred embodiments, it should therefore be noted that the genetically modified NK cell (especially where the cell expresses a CAR and CD16 or variant thereof) will exhibit three distinct modes of cell killing: General cytotoxicity which is mediated by activating receptors (e.g., an NKG2D receptor), ADCC which is mediated by antibodies bound to a target cell, and CAR mediated cytotoxicity. Particularly where such modified NK cells are administered to an individual with a therapeutic antibody, at least additive and more typically synergistic target specific killing are contemplated (with respect to cytotoxicity and ADCC). For example, the therapeutic antibody may target B7-H4, or may target a tumor associated antigen, a cancer associated antigen, or a tumor and cancer specific antigen.

Consequently, it should be appreciated that the manner of transfection will at least in part depend on the type of nucleic acid employed. Therefore, viral transfection, chemical transfection, mechanical transfection methods are all deemed suitable for use herein. For example, in one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In another embodiment, the vectors described herein allow for stable transfection of cells. In one embodiment, the vector allows incorporation of the transgene(s) into the genome of the cell. Preferably, such vectors have a positive selection marker and suitable positive selection markers include any genes that allow the cell to grow under conditions that would kill a cell not expressing the gene. Non-limiting examples include antibiotic resistance, e.g. geneticin (Neo gene from Tn5).

Alternatively, or additionally, the vector is a plasmid vector. In one embodiment, the vector is a viral vector. As would be understood by one of skill in the art, any suitable vector can be used, and suitable vectors are well-known in the art.

In still other embodiments, the cells are transfected with mRNA encoding the protein of interest (e.g., the CAR). Transfection of mRNA results in transient expression of the protein. In one embodiment, transfection of mRNA into NK-92 cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration. In at least some embodiments as described in more detail below, NK cell transfection with mRNA resulted in unexpectedly consistent and strong expression of the CAR at a high faction of transfected cells. Moreover, such transfected cells also exhibited a high specific cytotoxicity at comparably low effector to target cell ratios.

With respect to contemplated CARs it is noted that the NK or NK-92 cells will be genetically modified to express the CAR as a membrane bound protein exposing a portion of the CAR on the cell surface while maintaining the signaling domain in the intracellular space. Most typically, the CAR will include at least the following elements (in order): an extracellular binding domain, a hinge domain, a transmembrane domain, and an FcεRIγ signaling domain.

In preferred embodiments, the cytoplasmic domain of the CAR comprises or consists of a signaling domain of FcεRIγ. Notably, and as described in more detail below, the FcεRIγ signaling domain provide for substantially increased expression levels of the CAR as much as for significantly extended cytotoxicity over time. For example, the FcεRIγ signaling domain comprises or consists of or consists essentially of the amino acid sequence of SEQ ID NO:15. In some embodiments, the FcεRIγ cytoplasmic domain is the sole signaling domain. However, it should be appreciated that additional elements may also be included, such as other signaling domains (e.g., CD28 signaling domain, CD3ζ signaling domain, 4-1BB signaling domain, etc.). These additional signaling domains may be positioned downstream of the FcεRIγ cytoplasmic domain and/or upstream of the FcεRIγ cytoplasmic domain.

In some embodiments, the FcεRIγ signaling domain comprises or consists of or consists essentially of an amino acid sequence having at least about 85%, 90%, 95%, 96%, 97%, 98%, or 99% sequence homology to the amino acid sequence of SEQ ID NO:15, which may be encoded by a nucleic acid sequence having SEQ ID NO: 16. In alternative embodiments, the cytoplasmic domain of the CAR may also comprise a signaling domain of CD3 zeta (CD3ζ). In one embodiment, the cytoplasmic domain of the CAR consists of a signaling domain of CD3 zeta. In one embodiment, the CD3 zeta signaling domain comprises or consists of or consists essentially of the amino acid sequence of SEQ ID NO: 17. In some embodiments, the CD3 zeta signaling domain comprises or consists of or consists essentially of an amino acid sequence having at least about 85%, 90%, 95%, 96%, 97%, 98%, or 99% sequence homology to the amino acid sequence of SEQ ID NO:17, which may be encoded by a nucleic acid sequence having SEQ ID NO:18.

The CAR may comprise any suitable transmembrane domain. In one aspect, the CAR comprises a transmembrane domain of CD28. In one embodiment, the CD28 transmembrane domain comprises or consists of or consists essentially of the amino acid sequence of SEQ ID NO:19. In one embodiment, the CD28 transmembrane domain comprises or consists of or consists essentially of an amino acid sequence having at least about 85%, 90%, 95%, 96%, 97%, 98%, or 99% sequence homology to the amino acid sequence of SEQ ID NO:19. In other embodiments, the transmembrane domain may also be a 4-1BB transmembrane domain, which may be encoded by a nucleic acid sequence having SEQ ID NO:20.

The CAR may comprise any suitable hinge region. In one aspect, the CAR comprises a hinge region of CD8. In one embodiment, the CD8 hinge region comprises or consists of or consists essentially of the amino acid sequence of SEQ ID NO:5. In one embodiment, the CD8 hinge region comprises or consists of or consists essentially of an amino acid sequence having at least about 85%, 90%, 95%, 96%, 97%, 98%, or 99% sequence homology to the amino acid sequence of SEQ ID NO:5, which may be encoded by a nucleic acid sequence having SEQ ID NO:6.

Therefore, contemplated CARs will include a general structure of a desired antigen binding domain that is coupled to a hinge domain, which is coupled to a transmembrane domain, which is coupled to a signaling domain. Viewed from another perspective, contemplated CARs may have a desired binding domain that is then coupled to a hybrid protein that comprises, consists of, or essentially consists of a hinge domain, which is coupled to a transmembrane domain, which is coupled to a signaling domain. For example, such hybrid protein may have an amino acid sequence having at least about 85%, 90%, 95%, 96%, 97%, 98%, or 99% sequence homology to the amino acid sequence of SEQ ID NO:1, which may be encoded by a nucleic acid sequence having SEQ ID NO:2.

Most typically, but not necessarily, the extracellular binding domain of the CAR will be a scFv or other natural or synthetic binding portion that specifically binds B7-H4 as the antigen of interest. Therefore, especially suitable binding portions include small antibody fragments with single, dual, or multiple target specificities, beta barrel domain binders, phage display fusion proteins, etc. As will be readily appreciated, the scFv for an anti-B7-H4 may be identical to SEQ ID NO.21, or may have an amino acid sequence having at least about 85%, 90%, 95%, 96%, 97%, 98%, or 99% sequence homology to the amino acid sequence of SEQ ID NO.21 or to the amino acid sequences that define the CDR1, CDR2, and CDR3 regions within the VL and VH portions of the scFv. Such amino acid sequences may be encoded by a nucleic acid sequence having SEQ ID NO:22.

Consequently, contemplated CARs will target B7-H4 where expressed on the surface of a cancer cell and/or on a tumor associated immune competent cell (e.g., tumor-associated macrophage. For example, targeted cancers include ovarian cancer, renal cell carcinoma, melanoma, breast cancer, lung cancer, gastric cancer, colorectal cancer, pancreatic cancer, and prostate cancer.

Therefore, contemplated CARs will generally have a structure of an extracellular binding domain that is (directly) coupled to a hinge domain, which is (directly) coupled to a transmembrane domain, which is (directly) coupled to an FcεRIγ signaling domain. In still further contemplated aspects, contemplated CARs may also include one or more signaling domains in addition to or replacing the FcεRIγ signaling domain, and especially contemplated signaling domains include CD3ζ signaling domains, 4-1BB signaling domains, and CD28 signaling domains. With respect to the construction of contemplated CARs it should be recognized that CARs can be engineered in numerous manners as described, for example, in WO 2014/039523; US 2014/0242701; US 2014/0274909; US 2013/0280285 and WO 2014/099671, each of which is incorporated herein by reference in its entirety.

In still further contemplated aspects, and as noted above, NK cells may be further genetically modified to express one or more cytokines to so provide a selection marker where the cytokine and the CAR are encoded on the same recombinant nucleic acid, and/or to render the recombinant cells independent of exogenous IL-2. Therefore, in some aspects of the inventive subject matter, NK-92 cells are modified to express at least one cytokine. In particular, the at least one cytokine is IL-2, IL-12, IL-15, IL-18, IL-21, or a variant thereof. In preferred embodiments, the cytokine is IL-2 or a variant thereof and especially preferred variants include endoplasmic retention signals (e.g., human IL-2 as in SEQ ID NO:23, encoded by nucleic acid SEQ ID NO:24, or with ER retention signal as in SEQ ID NO:25, encoded by nucleic acid SEQ ID NO:26). For example, the IL-2 gene is cloned and expressed with a signal sequence that directs the IL-2 to the endoplasmic reticulum. This permits expression of IL-2 at levels sufficient for autocrine activation, but without releasing IL-2 extracellularly (e.g., *Exp Hematol*. 2005 February; 33(2):159-64.) Alternatively, expression of a cytokine (and especially IL-15) may also be such that the cytokine will be expressed in sufficient quantities to provide an autocrine growth signal to the recombinant cells, but also to allow at least some of the expressed IL-15 to be released from the cell, which will so provide an immune stimulatory signal. For example, such expression may be achieved using a human IL-15 sequence that includes both the signal peptide and an endoplasmic retention sequence. Exemplary amino acid and DNA sequences for an endoplasmic retained IL-15 are shown in SEQ ID NO:27 and SEQ ID NO:28, respectively.

Where desired, contemplated cells may also express a suicide gene. The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92 cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir. In another embodiment, the suicide gene is cytosine deaminase, which is toxic to cells in the presence of 5-fluorocytosine (e.g., Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood*. 1998 Jul. 15; 92(2):672-82). In a further embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther*. 2014; 14(3):236-46. In yet another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Of course, it should be noted that all of the recombinant proteins can be expressed from individual recombinant sequences. However, it is generally preferred that where multiple recombinant sequences are expressed (e.g., CAR, CD16, cytokine), coding regions may be arranged in a polycistronic unit with at least two or at least three coding regions encoding the recombinant proteins. For example, a tricistronic DNA or RNA construct (e.g., encoding the anti-B7-H4 CAR with an FcεRIγ signaling domain, a CD16$^{158V}$, and IL-2$^{ER}$ or IL15$^{ER}$) may be transfected into an NK or NK-92 cell. Therefore, transgenes can be engineered into an expression vector by any mechanism known to those of skill in the art. Where multiple transgenes are to be inserted into a cell, transgenes may be engineered into the same expression vector or a different expression vector. In some embodiments, the cells are transfected with mRNA encoding the transgenic protein to be expressed. In some embodiments, the cells are transfected with DNA encoding the transgenic protein to be expressed. Transgenes, mRNA and DNA can be introduced into the NK-92 cells using any transfection method known in the art, including, by way of non-limiting example, infection, viral vectors, electroporation, lipofection, nucleofection, or "gene-gun."

As will be readily apparent, contemplated genetically modified cells can be used for treatment of various diseases, and especially of various cancers where a diseased cell presents B7-H4 on the cell surface. Consequently, the inventors contemplate methods of treating patients with modified NK or NK-92 cells as described herein. In one embodiment, the patient is suffering from cancer (e.g., a tumor) and the modified NK-92 cell or cell line expresses an anti-B7-H4 CAR.

Contemplated modified NK or NK-92 cells can be administered to an individual by absolute numbers of cells. For example, the individual can be administered from about 1,000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per injection, or any ranges between any two of the numbers, end points inclusive. In other embodiments, modified NK-92 cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per kilogram of the individual, or any ranges between any two of the numbers, end points inclusive. In other embodiments, the total dose may calculated by m$^2$ of body surface area, including about $1\times10^{11}$, $1\times10^{10}$, $1\times10^9$, $1\times10^8$, $1\times10^7$, per m$^2$, or any ranges between any two of the numbers, end points inclusive. The average person is about 1.6 to about 1.8 m$^2$. In a preferred embodiment, between about 1 billion and about 3 billion NK-92 cells are administered to a patient.

Modified NK-92 cells, and optionally other anti-cancer agents can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the modified NK-92 cells express a suicide gene, the patient is administered an agent to trigger modified NK-92 cell death. In one embodiment, the agent is administered at a time point after administration of the modified NK-92 cells that is sufficient for the NK-92 cells to kill target cells.

In one embodiment, the modified NK-92 cells are irradiated prior to administration to the patient. Irradiation of NK-92 cells is described, for example, in U.S. Pat. No. 8,034,332, which is incorporated herein by reference in its entirety. In one embodiment, modified NK-92 cells that have not been engineered to express a suicide gene are irradiated.

Furthermore, it should be appreciated that contemplated treatments will also include administration of other immune therapeutic entities, and especially preferred immune therapeutic entities include a viral cancer vaccine (e.g., adenoviral vector encoding cancer specific antigens), a bacterial cancer vaccine (e.g., non-pyrogenic E. coli expressing one or more cancer specific antigens), a yeast cancer vaccine, N-803 (also known as ALT-803, ALTOR Biosciences), an antibody (e.g., binding to a tumor associated antigen or patient specific tumor neoantigen), a stem cell transplant (e.g., allogeneic or autologous), and a tumor targeted cytokine (e.g., NHS-IL12, IL-12 coupled to a tumor targeting antibody or fragment thereof).

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: CAR mRNA Preparation

DNA sequences encoding each variant of CD19CAR schematically depicted in FIG. 1 were designed in silico, synthesized de novo, and subcloned into a mRNA expression vector (GeneArt, Life Technologies). Ten micrograms (μg) of plasmid were linearized by digestion and purified using a QIAgen gel purification kit (QIAgen) according to manufacturer's instructions.

The linearized DNA was used as template for in vitro synthesis of mRNA using a T7 mMessage mMachine T7 Ultra transcription kit (ThermoFisher Scientific, Waltham, MA) according to the manufacturer's instructions. This kit includes a polyadenylation extension step that increases the length of the polyA tail of the mRNA and thus enhances stability in vivo.

Exemplary mRNAs for six distinct CD19CAR variants were prepared, with a green fluorescent protein (GFP) mRNA prepared as a negative control. More particularly, all of the CAR variants contained an extracellular domain comprising an anti-CD19 scFv region (αCD19-scFv), a hinge region from CD8, and a transmembrane domain from CD28. The intracellular domains of the CD19CARs were as follows and are schematically shown in FIG. 1: CAR 3z contained a CD3ζ signaling domain; CAR FcRe contained a FcεRIγ signaling domain; CAR 28_3z contained a CD28 signaling domain fused to a CD3ζ signaling domain; CAR BB_3z contained a 4-1BB signaling domain fused to a CD3ζ signaling domain; CAR 28_BB_3z contained a CD28 signaling domain fused to a 4-1BB signaling domain fused to a CD3ζ signaling domain; CAR BB_3z_28 contained a 4-1BB signaling domain fused to a CD3ζ signaling domain fused to a CD28 signaling domain.

More particularly, the 1$^{st}$ generation CAR with CD3ζ signaling domain of FIG. 1 had a nucleic acid sequence of SEQ ID NO:29. The 1$^{st}$ generation CAR with a FcεRIγ signaling domain nucleic had a nucleic acid sequence of SEQ ID NO:30.

Example 2: Electroporation of NK-92 Cells With CD19CAR mRNA

NK-92 cells were grown in growth medium supplemented with 5% Human AB Serum (Valley Biomedical, Winchester, VA) and 500 IU/mL IL-2 (Prospec, Rehovot, Israel). Cells were electroporated with mRNA using the Neon™ electroporation device (Life Technologies, Carlsbad, CA). Electroporated cells were maintained in medium (same as above) for 20 hours (h).

Figure 2A:
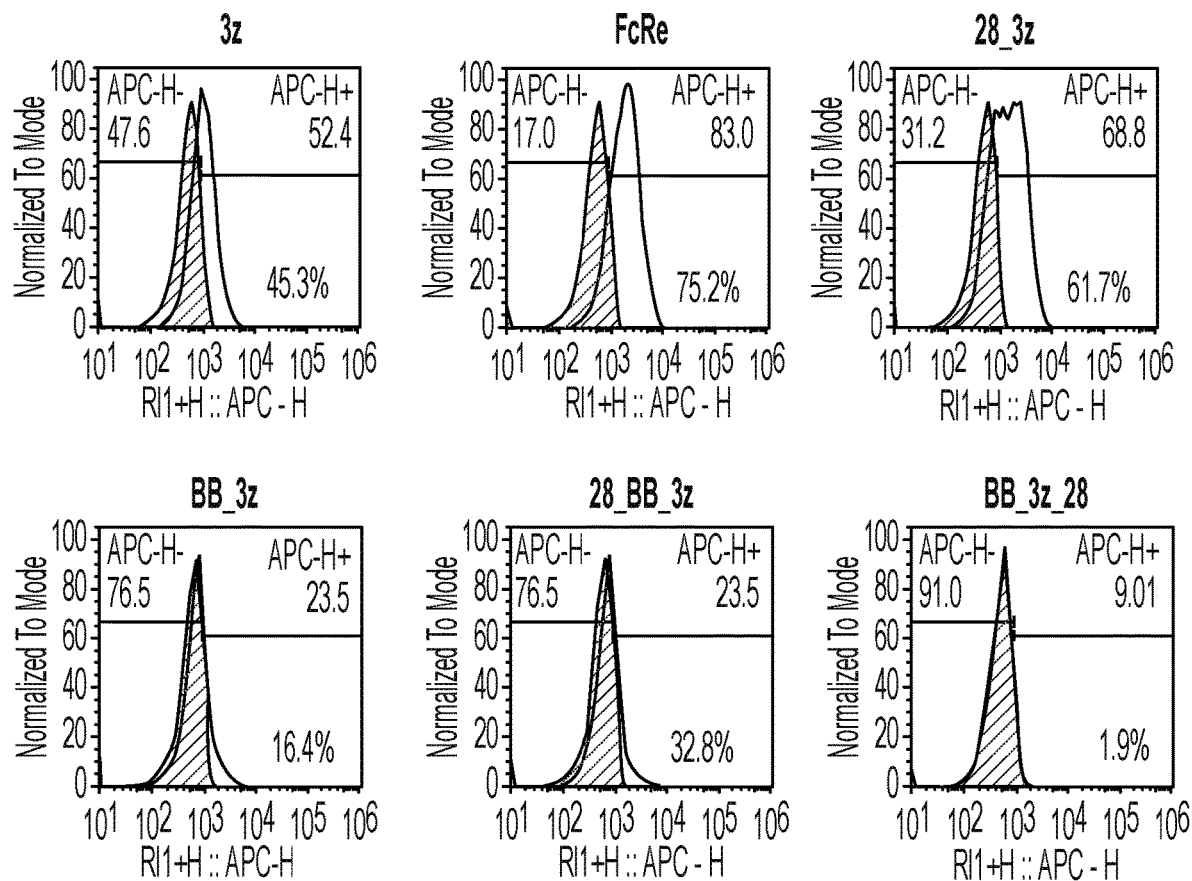
FIG. 2A are exemplary results for the percentage of NK-92 cells expressing the CD19-CAR of FIG. 1 after transfection with CD19-CAR mRNA as determined by flow cytometry with an anti-scFv antibody labeled with eF660.
Figure 2B:
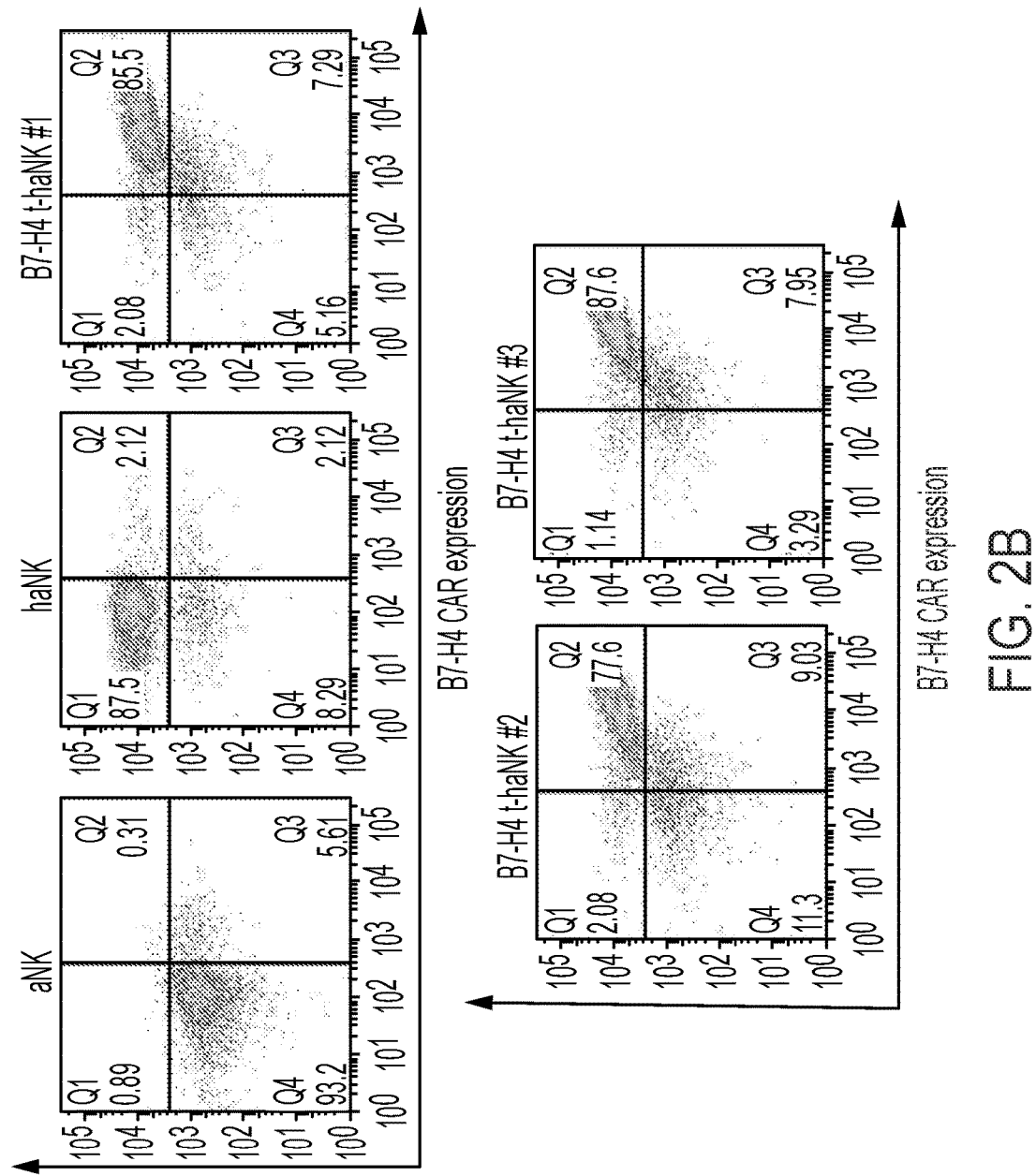
FIG. 2B are exemplary results for the percentage of NK-92 cells expressing CD16 and the anti-B7-H4 FcεRIγ-containing CAR (as in FIG. 1 but with anti-B7-H4 scFv) after transfection with linear tricistronic anti-B7-H4 CAR DNA.

The CD19CAR expression on the NK-92 cell surface was determined by flow cytometry using anti-scFv antibody labeled with eF660 (eBioscience, San Diego, CA). FIG. 2A shows the % expression of the indicated CAR in the NK-92 cell population. Similarly, expression was confirmed for constructs encoding the anti-B7-H4 CAR, endoplasmically retained IL-2, and CD16. Here, FIG. 2B shows the % co-expression of the anti-B7-H4 CAR with CD16 in three independent clonal populations of hanK cells expressing the anti-B7-H4 CAR, endoplasmically retained IL-2, and CD16. As can be taken from FIGS. 2A and 2B, CAR constructs with an FcRe portion unexpectedly had the highest percentage of cells (75.2%) expressing CD19CAR at the cell surface, and had superior and consistent co-expression with CD16.

Example 3: Durability of CAR Surface Expression of NK-92 Cells Expressing Various CAR Constructs The inventors next quantified expression levels for the various CAR constructs to investigate durability of expression over time. For these and the following experiments, the CAR, CD16, and erIL-2 were expressed from a tricistronic construct as is shown in more detail below.

Figure 3:
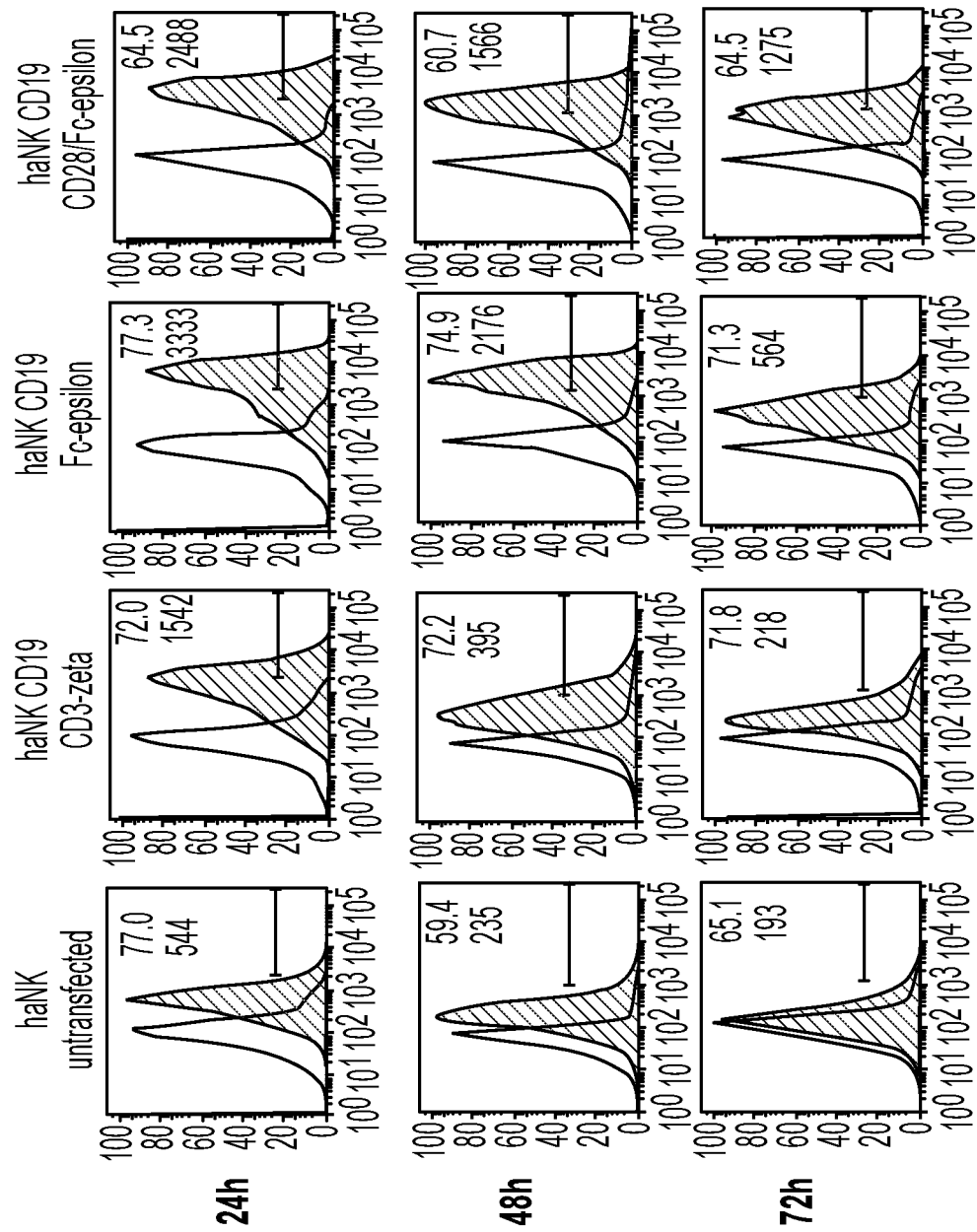
FIG. 3 shows exemplary results for surface expression of exemplary CAR constructs on haNK cells transfected with CAR mRNA constructs as indicated at various time points. All CAR constructs tested show detectable expression for up to 72 h under the conditions used with CD8 Hinge-Fc-epsilon CAR having the longest duration of expression.

As can be seen from the results in FIG. 3, NK-92 cells transfected with the different CAR constructs expressed detectable levels of the respective CARs on the cell surface for up to 72 hours in all cases. Unexpectedly, however, and as can be readily seen from FIG. 5, the CAR constructs that comprised the Fc-epsilon cytoplasmic signaling domain had substantially longer durations of expression. Notably, it was also observed that addition of one or more signaling domains in addition to the FcεRIγ signaling domain (e.g., CD28 signaling domain in the example presented here) did not adversely affect the duration of expression. Indeed, in the CAR having the FcεRIγ signaling domain and the CD28 signaling domain duration of expression was even further increased over time, whereas CAR constructs with a CD3-zeta signaling domain had a dramatic reduction in expression at the 72 hour mark, and even before then. Moreover, as can also be seen from the results in FIG. 5, the quantity of expression of CAR constructs having the FcεRIγ signaling domain was also initially significantly higher than corresponding constructs with a CD3-zeta signaling domain.

Example 4. Map of Tricistronic Expression Cassette

Figure 4:
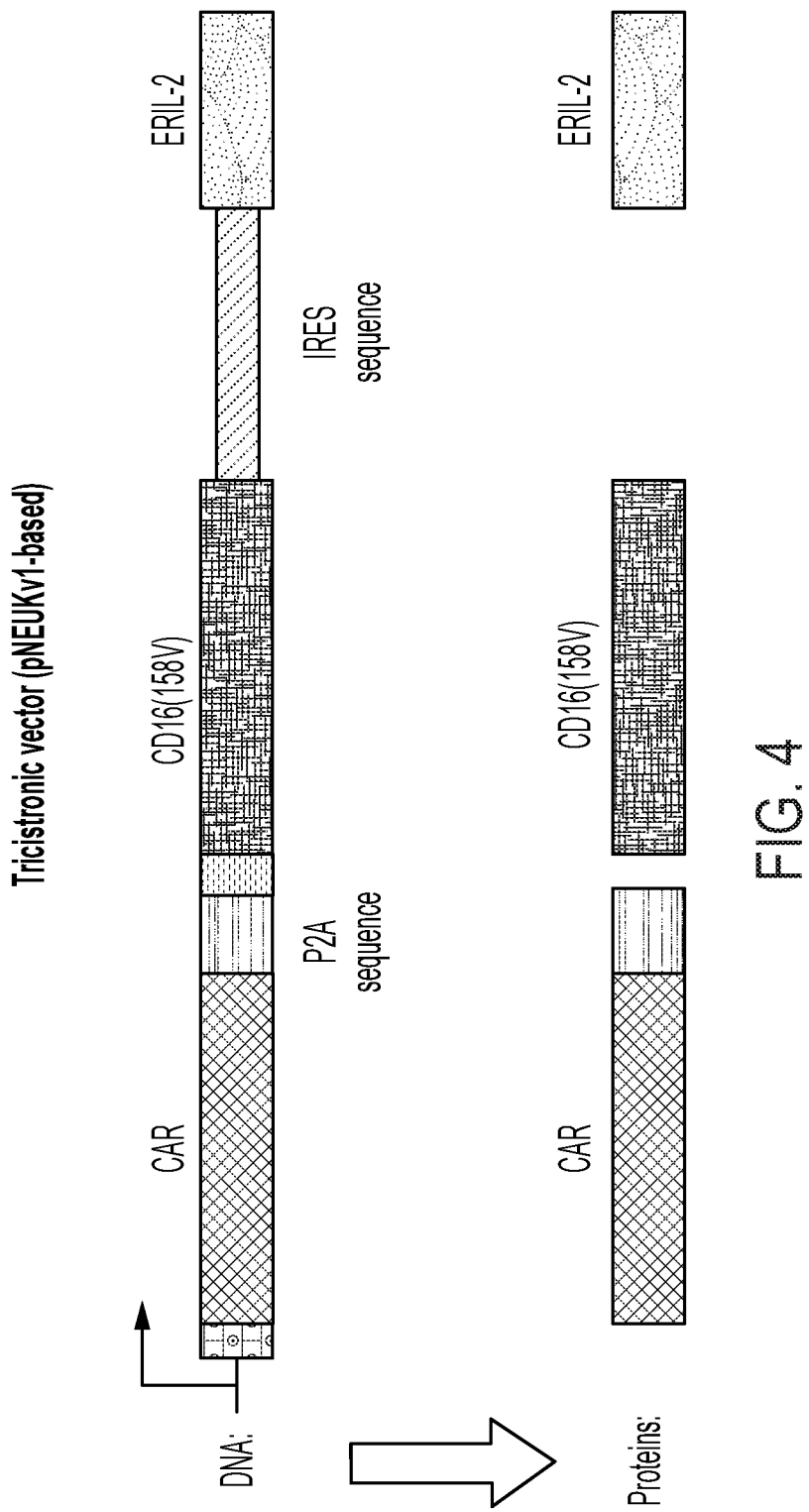
FIG. 4 is an exemplary schematic of a recombinant tricistronic DNA construct and corresponding protein products.
Figure 5:
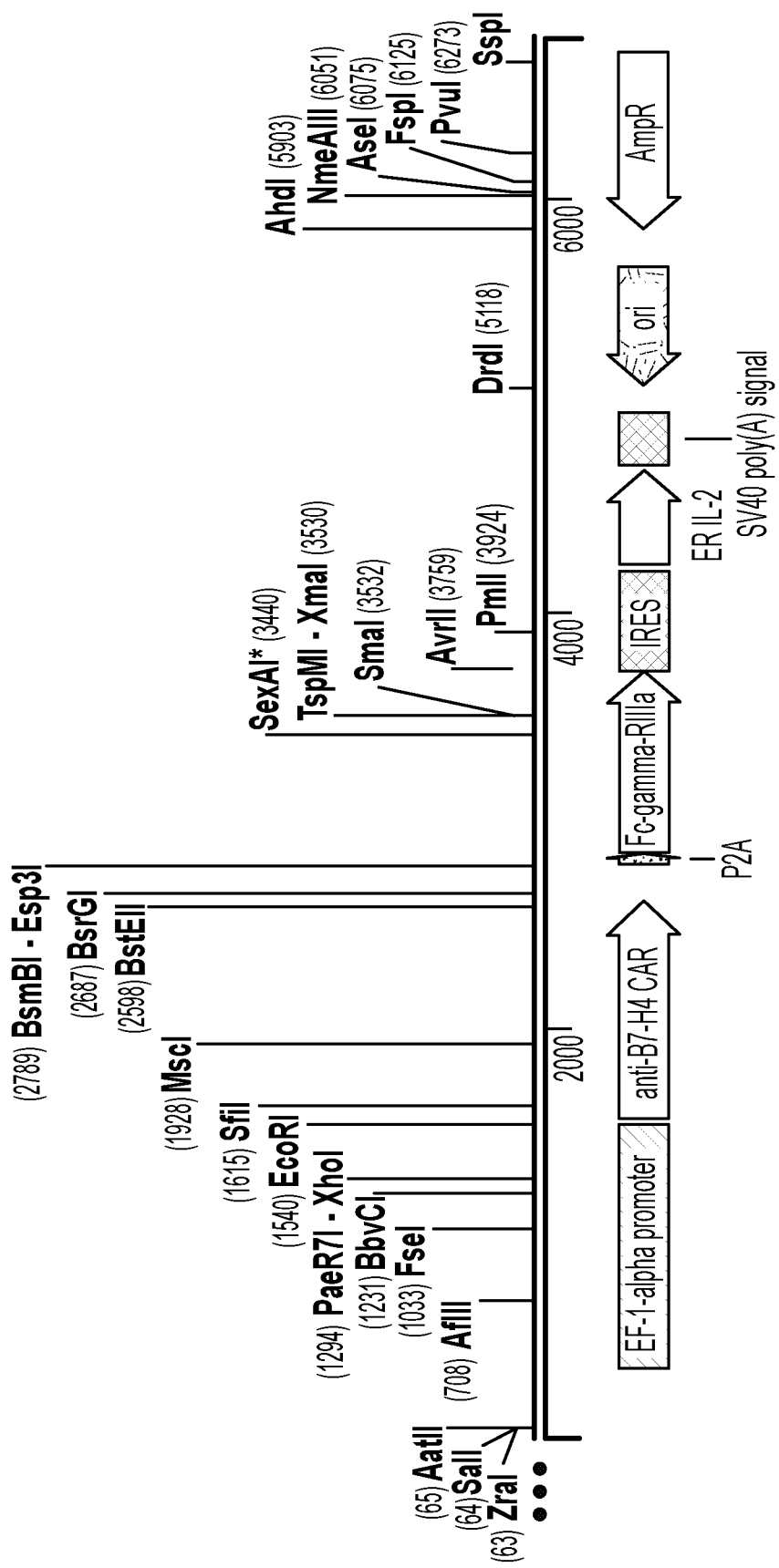
FIG. 5 is an exemplary representation of a recombinant tricistronic DNA construct of FIG. 4.

FIG. 4 shows diagrammatically exemplary DNA and protein products produced by a representative tricistronic expression cassette, and FIG. 5 illustrates an exemplary linearized version of a plasmid with such expression cassette.

Example 5: B7-H4-CAR With FcεRIγ Signaling Domain

In this example, the inventors constructed a $1^{st}$ generation CARs with a FcεRIγ signaling domain that included an anti-B7-H4 scFv coupled to a CD8 hinge, that in turn was coupled to a CD28 transmembrane domain, which was coupled to a FcεRIγ signaling domain. The so constructed anti-B7-H4-CAR had an amino acid sequence of SEQ ID NO:1 and a nucleic acid sequence of SEQ ID NO:2.

Example 6: B7-H4-CAR Cytotoxicity Against K562 Cells

Figure 6:
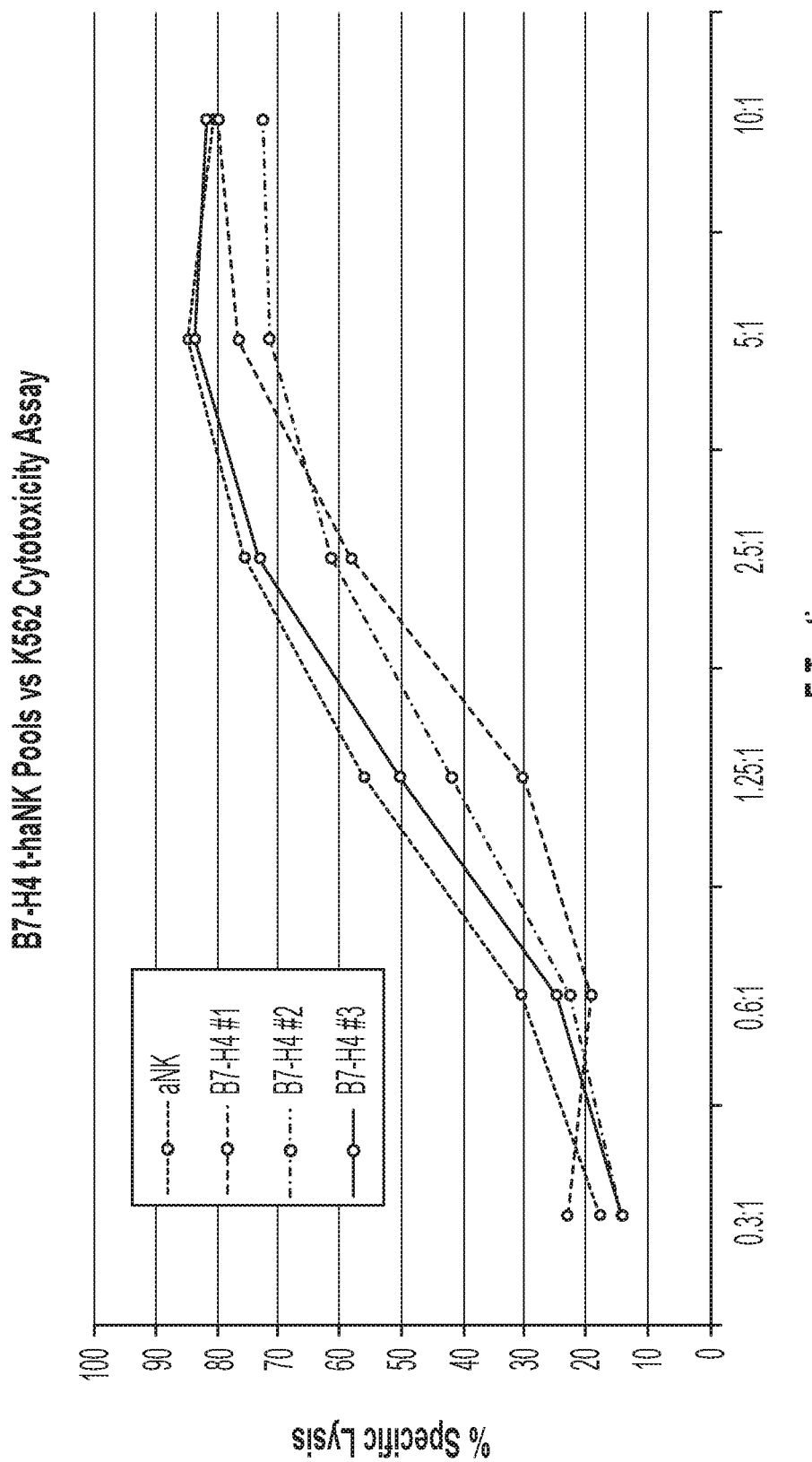
FIG. 6 shows exemplary results for cytotoxicity of NK cells expressing an anti-B7-H4 FcεRIγ-containing CAR against K562 cells (NK target cells).

In the following example, the inventors used the $1^{st}$ generation anti-B7-H4-CAR of Example 5 to determine cytotoxicity against K562 cells (human immortalized myelogenous leukemia cells recognized by NK cells). The anti-B7-H4-CAR included a FcεRIγ signaling domain with an anti-B7-H4 scFv coupled to a CD8 hinge, that in turn was coupled to a CD28 transmembrane domain, which was coupled to a FcεRIγ signaling domain. Three different recombinant NK-92 cell lines (#1-#3, selected after transfection in the absence of exogenous IL-2) were tested using aNK cells as control. As can be readily taken from the results in FIG. 6, recombinant NK-92 cells expressing anti-B7-H4-CAR, CD16, and erIL-2 had significant cytotoxicity at slightly lower levels as compared to aNK cells not expressing anti-B7-H4-CAR, CD16, and erIL-2.

Example 7: B7-H4-CAR Cytotoxicity Against MX1 Cells

Figure 7:
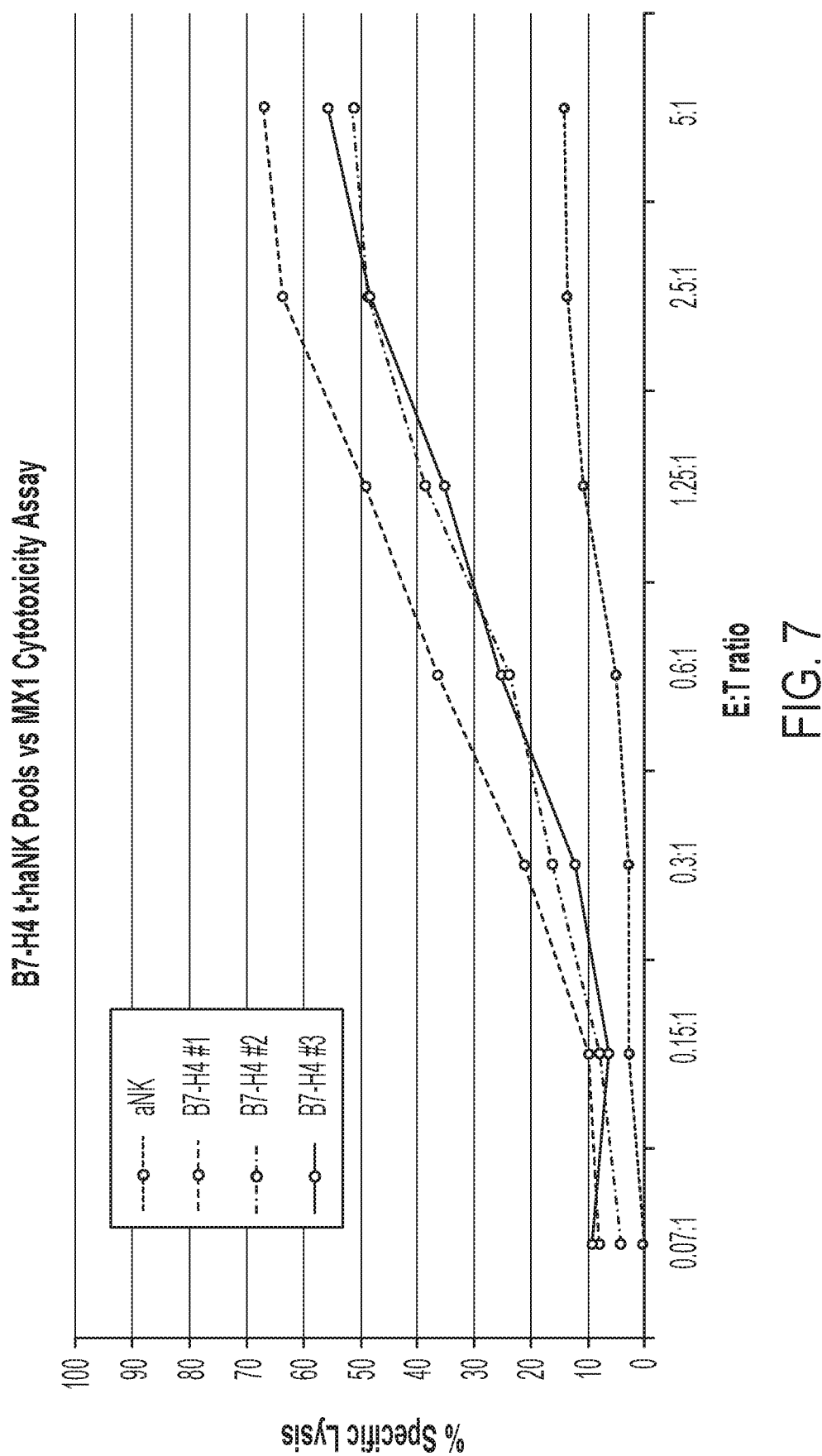
FIG. 7 shows exemplary results for cytotoxicity of NK cells expressing an anti-B7-H4 FcεRIγ-containing CAR against MX1 cells (cells expressing B7-H4).

In this example, the inventors used the $1^{st}$ generation anti-B7-H4-CAR of Example 5 to determine cytotoxicity against MX1 cells (a human breast carcinoma cell line expressing B7-H4). The anti-B7-H4-CAR included a FcεRIγ signaling domain with an anti-B7-H4 scFv coupled to a CD8 hinge, that in turn was coupled to a CD28 transmembrane domain, which was coupled to a FcεRIγ signaling domain. Once more, three different recombinant NK-92 cell lines (#1-#3, selected after transfection in the absence of exogenous IL-2) were tested using aNK cells as control. Notably, all recombinant NK-93 cells expressing anti-B7-H4-CAR, CD16, and erIL-2 had significant CAR-mediated cytotoxicity while the aNK control cells had only marginal cytotoxicity, even at very high effector to target ratios as is shown in FIG. 7. Therefore, it should be appreciated that the recombinant NK cells expressing an anti-B7-H4 CAR had significant and target specific cytotoxicity.

Example 8: B7-H4-CAR Cytotoxicity Against SUP-B15 Cells

Here, the inventors used once more the $1^{st}$ generation anti-B7-H4-CAR of Example 5 to determine cytotoxicity against a variant of the SUP-B15 cell line (an acute lymphoblastic leukemia cell line modified to express CD20 and otherwise resistant to NK-92-mediated cytotoxicity). The anti-B7-H4-CAR included a FcεRIγ signaling domain with an anti-B7-H4 scFv coupled to a CD8 hinge, that in turn was coupled to a CD28 transmembrane domain, which was coupled to a FcεRIγ signaling domain. Once more, three different recombinant NK-92 cell lines (#1-#3, selected after transfection in the absence of exogenous IL-2) were tested using aNK cells as control. To test ADCC capacity, a CD20-specific antibody (rituxan) was used while a HER2 specific antibody was used as negative control. Control cells were haNK cells that expressed CD16, but did not express a CAR.

Figure 8:
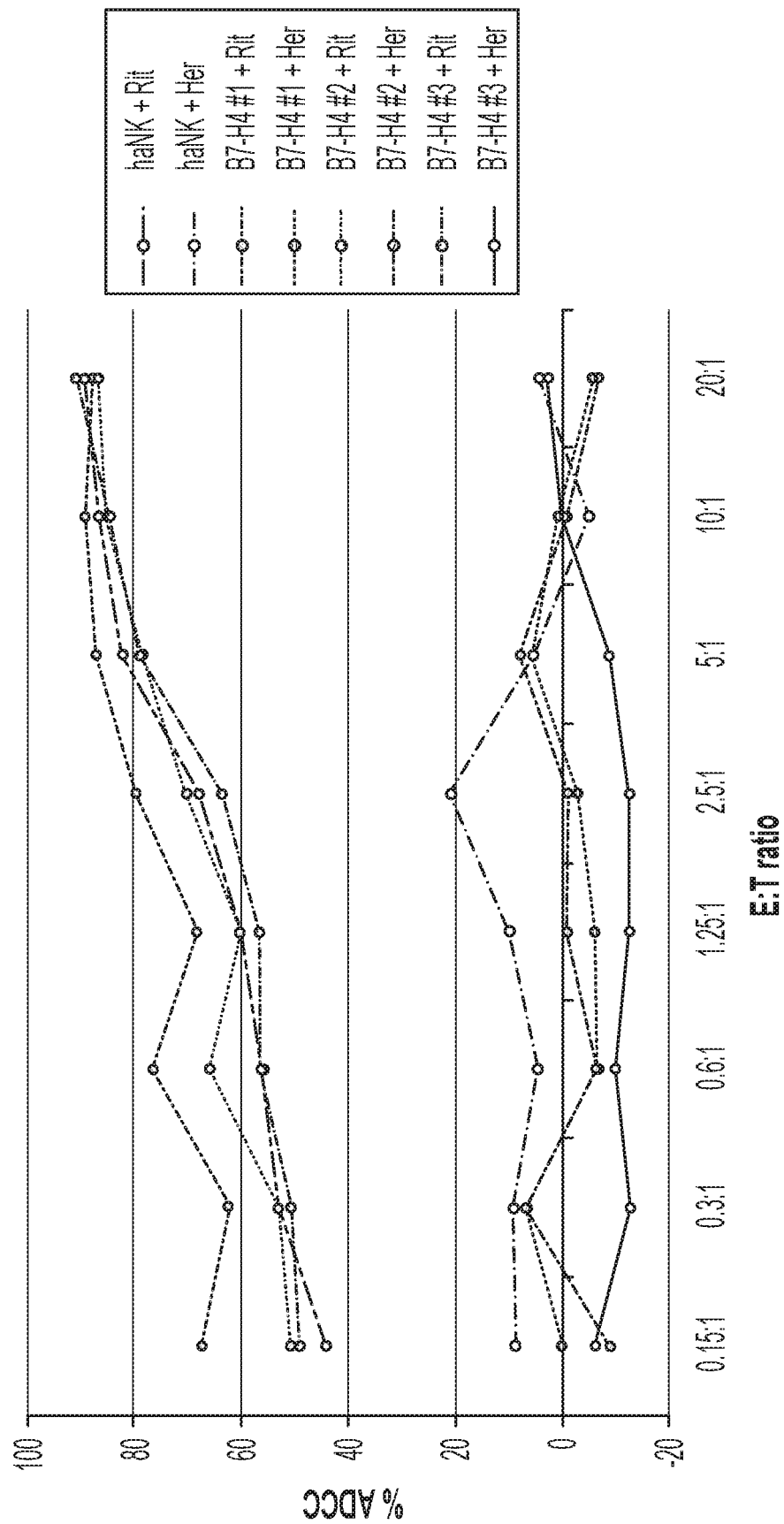
FIG. 8 shows exemplary results for ADCC of NK cells expressing an anti-B7-H4 FcεRIγ-containing CAR against a variant of SUP-B15 cells expressing CD20 in the presence of on-target (rituxan) and off-target (herceptin) antibodies.

As can be seen from FIG. 8, all recombinant NK-92 cells expressing anti-B7-H4-CAR, CD16, and erIL-2 had significant antibody-mediated cytotoxicity that was substantially on par with haNK control cells where the antibody used was on-target, with substantially no ADCC with antibodies that were off-target. Therefore, it should be appreciated that the recombinant NK cells expressing an anti-B7-H4 CAR had significant and target specific ADCC. As such, all target specific functions of the recombinant NK cells expressing anti-B7-H4-CAR, CD16, and erIL-2 were confirmed. Moreover, the expression levels, duration, and CAR-mediated cytotoxicity were superior to conventional CAR constructs. As such, recombinant NK cells with anti-B7-H4-CAR, CD16, and erIL-2 are unexpectedly improved over other recombinant cells expressing an anti-B7-H4-CAR.

Of course, it should be recognized that for all nucleic acid sequences provided herein the corresponding encoded proteins are also expressly contemplated herein. Likewise, for all amino acid sequences, corresponding nucleic acids sequences are also contemplated herein (with any codon usage).

All patent applications, publications, references, and sequence accession numbers cited in the present specification are hereby incorporated by reference in their entirety.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

It is understood that all numerical values described herein (e.g., pH, temperature, time, concentration, amounts, and molecular weight, including ranges) include normal variation in measurements encountered by one of ordinary skill in the art. Thus, numerical values described herein include variation of +/−0.1 to 10%, for example, +/−0.1%, 0.5%, 1%, 2%, 3%, 4%, 5%, 6%, 7%, 8%, 9%, or 10%. It is to be understood, although not always explicitly stated, that all numerical designations may be preceded by the term "about." Thus, the term about includes variation of +/−0.1 to 10%, for example, +/−0.1%, 0.5%, 1%, 2%, 3%, 4%, 5%, 6%, 7%, 8%, 9%, or 10% of the numerical value. It is also to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein include the end points of the range, and include all values between the end points of the range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest (hereafter, "NK-92™ cells"). The immortal NK cell line was originally obtained from a patient having non-Hodgkin's lymphoma. Unless indicated otherwise, the term "NK-92™" is intended to refer to the original NK-92 cell lines as well as NK-92 cell lines that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™ NK-92™-CD16, NK-92™-CD16-γ, NK-92™-CD16-ζ, NK-92™-CD16(F176V), NK-92™ MI, and NK-92™ CI. NK-92 cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK™ cells"). The term "haNK" refers to natural killer cells derived from the highly potent unique cell line described in Gong et al. (1994), rights to which are owned by NantKwest, modified to express CD16 on the cell surface (hereafter, "CD16+NK-92™ cells" or "haNK® cells"). In some embodiments, the CD16+NK-92™ cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92™ cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+NK-92™ cells" or "t-haNK™ cells"). In some embodiments, the t-haNK™ cells express a high affinity CD16 receptor on the cell surface.

A "modified NK-92 cell" refers to an NK-92 cell that expresses an exogenous gene or protein, such as an Fc receptor, a CAR, a cytokine (such as IL-2 or IL-15), and/or a suicide gene. In some embodiments, the modified NK-92 cell comprises a vector that encodes for a transgene, such as an Fc receptor, a CAR, a cytokine (such as IL-2 or IL-15), and/or a suicide gene. In one embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be prevented from proliferating by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A is a low affinity Fc receptor bind to IgG antibodies and activate ADCC. FCγRIII-A are typically found on NK cells. NK-92 cells do not express FCγRIII-A. Fc-epsilon receptors (FcR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The term "virus-specific antigen" as used herein refers to antigens that are present on a virus-infected cell but not detectable on a normal cell derived from the same tissue or lineage as the virus-infected cell. In one embodiment, a virus-specific antigen is a viral protein expressed on the surface of an infected cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous amino acid sequence has no more than 15, nor more than 10, nor more than 5 or no more than 3 conservative amino acid substitutions. In some embodiments, a nucleotide or amino acid sequence has at least 60%, at least 65%, at least 70%, at least 80%, or at least 85% or greater percent identity to a sequence described herein. In some embodiments, a nucleotide or amino acid sequence has at least 90%, 91%, 92%, 93%, 94%, 95%, 96%, 97%, 98% or 99% identity to a sequence described herein. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). Algorithms suitable for determining percent sequence identity include the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (see the internet at ncbi.nlm.nih.gov). The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=-4.

In some embodiments, a nucleic acid sequence is codon optimized for expression in a particular species, for example, a mouse sequence can be codon optimized for expression in humans (expression of the protein encoded by the codon-optimized nucleic acid sequence). Thus, in some embodiments, a codon-optimized nucleic acid sequence has at least 60%, at least 65%, at least 70%, at least 80%, or at least 85% or greater percent identity to a nucleic acid sequence described herein. In some embodiments, a codon-optimized nucleic acid sequence acid sequence has at least 90%, 91%, 92%, 93%, 94%, 95%, 96%, 97%, 98% or 99% identity to a sequence described herein.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL)—in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92 cells to recognize and kill a tumor cell (i.e., target cell). The term "targeted" in this context refers, for example, to the ability of a CAR expressed by the NK-92 cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

What is claimed is:

1. A genetically modified anti-B7-H4 CAR NK cell, comprising:
a recombinantly expressed cytokine, wherein the recombinantly expressed cytokine comprises IL-2 or IL-15;
a recombinantly expressed CD16;
a membrane bound recombinantly expressed anti-B7-H4 chimeric antigen receptor (CAR) that comprises in a single polypeptide chain an extracellular binding domain, a hinge domain, a transmembrane domain, and a FcεRIγ signaling domain, wherein the extra cellular binding domain comprises an anti-B7-H4 scFv comprising SEQ ID NO: 21, and wherein the anti-B7-H4 CAR has at least 90% sequence homology to amino acid sequence of SEQ ID NO:1;
wherein the recombinantly expressed cytokine, the recombinantly expressed CD16, and the anti-B7-H4 CAR are expressed from an expression cassette of a plasmid that is transfected into the NK cell; and
wherein the NK cell is an NK-92 cell.

2. The genetically modified NK cell of claim 1 wherein the recombinantly expressed cytokine comprises an endoplasmic retention sequence.

3. The genetically modified NK cell of claim 1 wherein the recombinantly expressed CD16 is a high-affinity CD16 variant having a 158V mutation.

4. The genetically modified NK cell of claim 1 wherein the extracellular binding domain comprises a scFv.

5. The genetically modified NK cell of claim 1 wherein recombinantly expressed cytokine, the recombinantly expressed CD16, and the recombinantly expressed CAR are expressed from a tricistronic recombinant nucleic acid.

6. The genetically modified NK cell of claim 1 wherein the recombinantly expressed cytokine and/or the recombinantly expressed CD16 is expressed from a recombinant nucleic acid that is integrated into the genome of the NK cell.

7. A recombinant nucleic acid plasmid, comprising:
a first sequence portion encoding a cytokine, wherein the cytokine comprises IL-2 or IL-15;
a second sequence portion encoding a CD16;
a third sequence portion encoding an anti-B7-H4 CAR that comprises in a single polypeptide chain an extracellular binding domain, a hinge domain, a transmembrane domain, and a FcεRIγ signaling domain, wherein the extra cellular binding domain comprises an anti-B7-H4 scFv comprising SEQ ID NO: 21, and wherein the anti-B7-H4 CAR has at least 90% sequence homology to amino acid sequence of SEQ ID NO:1;
wherein the first, second, and third sequence portions encoding the cytokine, the recombinantly expressed CD16, and the anti-B7-H4 CAR, respectively, form an expression cassette on the plasmid.

8. The recombinant nucleic acid of claim 7 wherein the expression cassette is a tricistronic DNA.

9. The recombinant nucleic acid of claim 7 wherein the cytokine is IL-2.

10. The recombinant nucleic acid of claim 7 wherein the cytokine comprises an endoplasmic retention sequence.

11. The recombinant nucleic acid of claim 7 wherein the CD16 is a high-affinity CD16 variant having a 158V mutation.

12. The recombinant nucleic acid of claim 7 wherein the extracellular binding domain comprises a scFv.

13. The recombinant nucleic acid of claim 7 wherein the hinge domain and/or the transmembrane domain comprise a CD8 hinge domain and/or a CD28 transmembrane domain.

14. A recombinant cell comprising the recombinant nucleic acid of claim 7.

15. The recombinant cell of claim 14 wherein the cell is a bacterial cell.

16. The recombinant cell of claim 14 wherein the cell is an autologous NK cell.

17. The recombinant cell of claim 16 wherein the NK cell is an NK-92 cell that is optionally genetically modified.

18. A method of treating cancer in a patient in need thereof, comprising administering to the patient a therapeutically effective amount of the genetically modified NK cells of claim 1, thereby treating the cancer.

19. The method of claim 18 further comprising a step of administering at least one additional therapeutic entity selected from the group consisting of a viral cancer vaccine, a bacterial cancer vaccine, a yeast cancer vaccine, N-803, a bi-specific engager, an antibody, a stem cell transplant, a primary NK cell, and a tumor targeted cytokine.

20. The method of claim 18, wherein the cancer is selected from leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

21. A method of administering NK cells to an individual, comprising administering a first composition comprising NK cells that express a B7-H4 CAR, wherein the extra cellular binding domain of the CAR comprises an anti-B7-H4 scFv comprising SEQ ID NO: 21 and wherein the anti-B7-H4 CAR has at least 90% sequence homology to amino acid sequence of SEQ ID NO:1, and a second composition comprising primary NK cells.

* * * * *